United States Patent
Igarashi

(10) Patent No.: US 12,213,647 B2
(45) Date of Patent: Feb. 4, 2025

(54) OBJECTIVE OPTICAL SYSTEM, IMAGE PICKUP APPARATUS, AND ENDOSCOPE

(71) Applicant: OLYMPUS CORPORATION, Hachioji (JP)

(72) Inventor: Tsutomu Igarashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 380 days.

(21) Appl. No.: 17/884,351

(22) Filed: Aug. 9, 2022

(65) Prior Publication Data
US 2022/0386857 A1 Dec. 8, 2022

Related U.S. Application Data

(63) Continuation of application No. PCT/JP2020/006586, filed on Feb. 19, 2020.

(51) Int. Cl.
 *A61B 1/00* (2006.01)
 *G02B 23/24* (2006.01)
(52) U.S. Cl.
 CPC ........ *A61B 1/00188* (2013.01); *G02B 23/243* (2013.01)
(58) Field of Classification Search
 None
 See application file for complete search history.

(56) References Cited

U.S. PATENT DOCUMENTS

| | | | | |
|---|---|---|---|---|
| 1,593,786 A | * | 7/1926 | Worthington | G02B 13/0095 359/767 |
| 4,354,734 A | * | 10/1982 | Nakahashi | G02B 23/243 385/119 |
| 5,083,223 A | * | 1/1992 | Igarashi | G02B 23/243 359/708 |
| 5,119,238 A | * | 6/1992 | Igarashi | G02B 9/34 359/716 |

(Continued)

FOREIGN PATENT DOCUMENTS

| JP | S5625709 A | 3/1981 |
|---|---|---|
| JP | 2015127741 A | 7/2015 |

OTHER PUBLICATIONS

International Search Report (ISR) (and English translation thereof) dated Jul. 4, 2020, issued in International Application No. PCT/JP2020/006586.

(Continued)

*Primary Examiner* — John P Leubecker
*Assistant Examiner* — Jae Woo
(74) *Attorney, Agent, or Firm* — Holtz, Holtz & Volek PC

(57) ABSTRACT

There is provided an objective optical system that is easy to produce, capable of forming optical images that can be observed without difficulties while small in size. The objective optical system includes, in order from the object side, a flat plate OP1, an aperture stop S, and a substantially hemispherical planoconvex lens L1 having an outer diameter substantially equal to the outer diameter of the flat plate. The flat plate and the planoconvex lens L1 are cemented (Continued)

together with the aperture stop between. The objective optical system satisfies the following conditional expressions (1), (2), and (3):

$$0.3 < IH/Dp < 0.45 \qquad (1)$$

$$1.7 < 1 + Dp \times \omega r/(2 \times IH) < 2.1 \qquad (2)$$

$$0.9 < NL/(1 + Dp \times \omega r/(2 \times IH)) < 1.1 \qquad (3).$$

18 Claims, 8 Drawing Sheets

(56) References Cited

U.S. PATENT DOCUMENTS

| | | | | |
|---|---|---|---|---|
| 5,177,605 A * | 1/1993 | Takahashi | ............... | A61B 1/05 359/359 |
| 7,027,231 B2 * | 4/2006 | Miyano | ............... | G02B 23/243 359/784 |
| 9,915,818 B2 | 3/2018 | Lin et al. | | |
| 2005/0200977 A1 * | 9/2005 | Tesar | ............... | G02B 27/0025 359/754 |
| 2016/0274349 A1 * | 9/2016 | Lin | ............... | G02B 23/243 |
| 2019/0121117 A1 * | 4/2019 | Amanai | ............ | G02B 23/2469 |
| 2021/0333526 A1 * | 10/2021 | Imaoka | ............... | G03B 21/14 |
| 2022/0386857 A1 * | 12/2022 | Igarashi | ............ | A61B 1/00188 |

OTHER PUBLICATIONS

Written Opinion dated Jul. 4, 2020, issued in International Application No. PCT/JP2020/006586.

International Preliminary Report on Patentability (IPRP) (and English language translation thereof) dated Sep. 1, 2022, issued in International Application No. PCT/JP2020/006586.

* cited by examiner

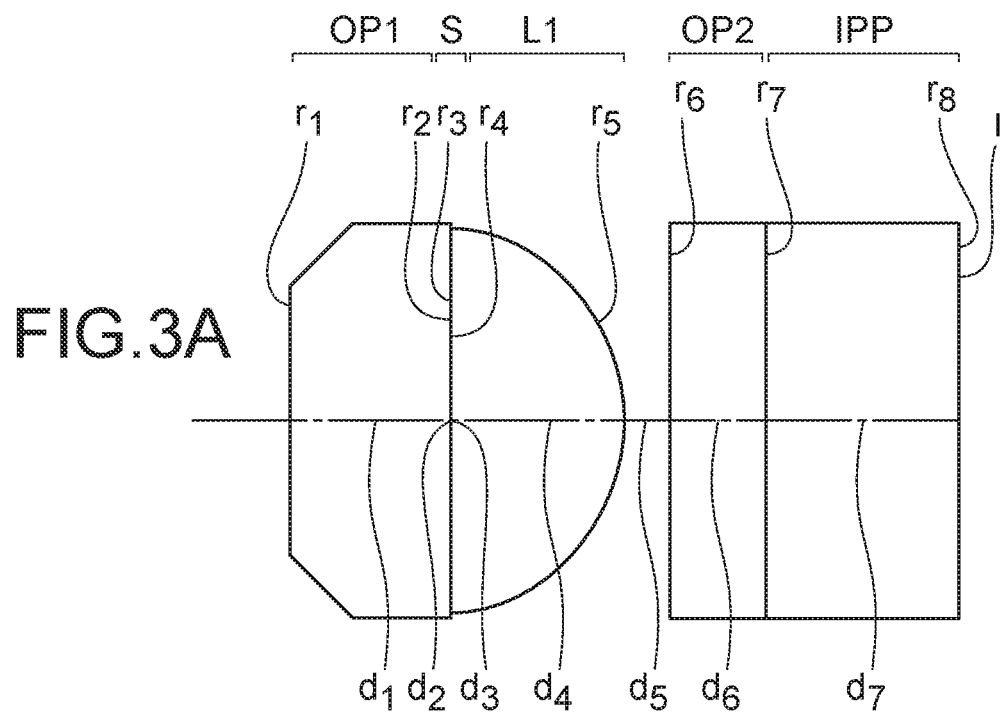
FIG.3A
FIG.3B  FIG.3C  FIG.3D  FIG.3E
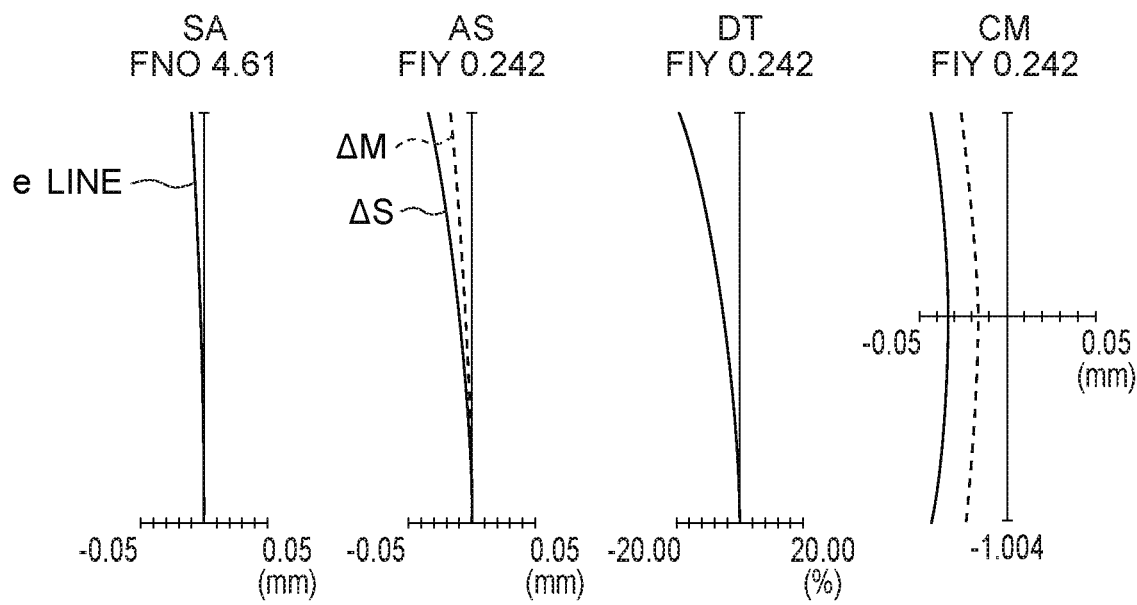

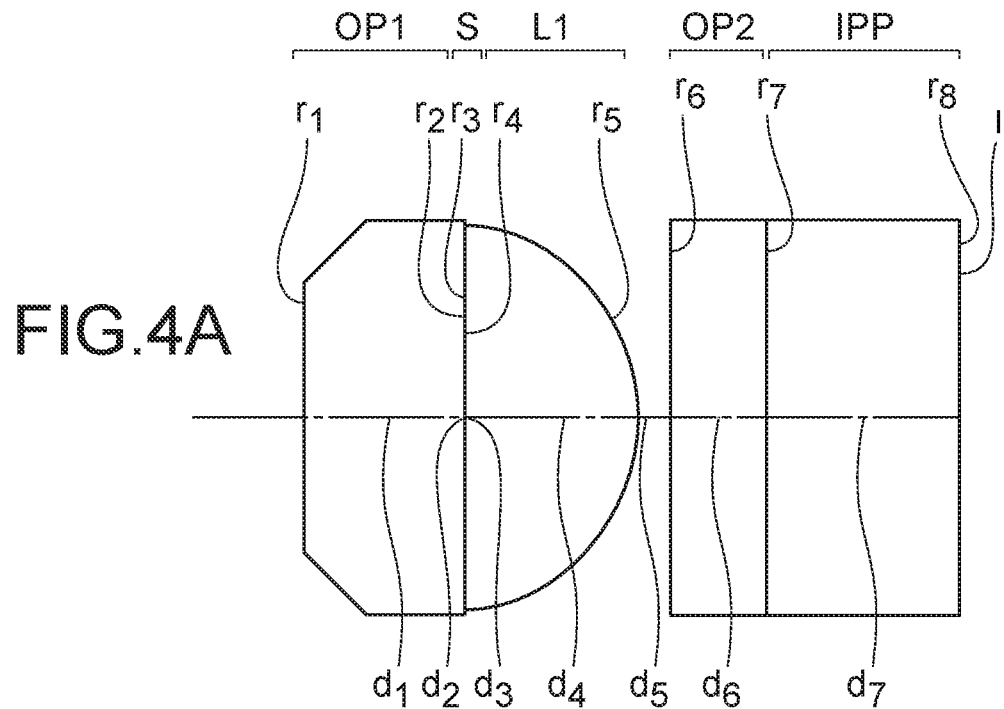
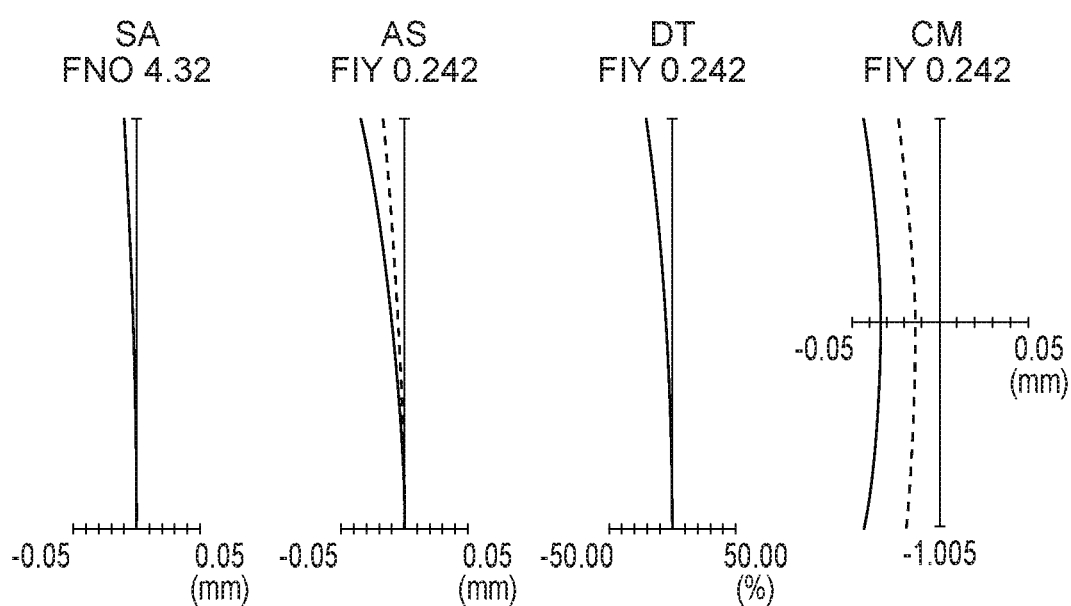
FIG.4B  FIG.4C  FIG.4D  FIG.4E

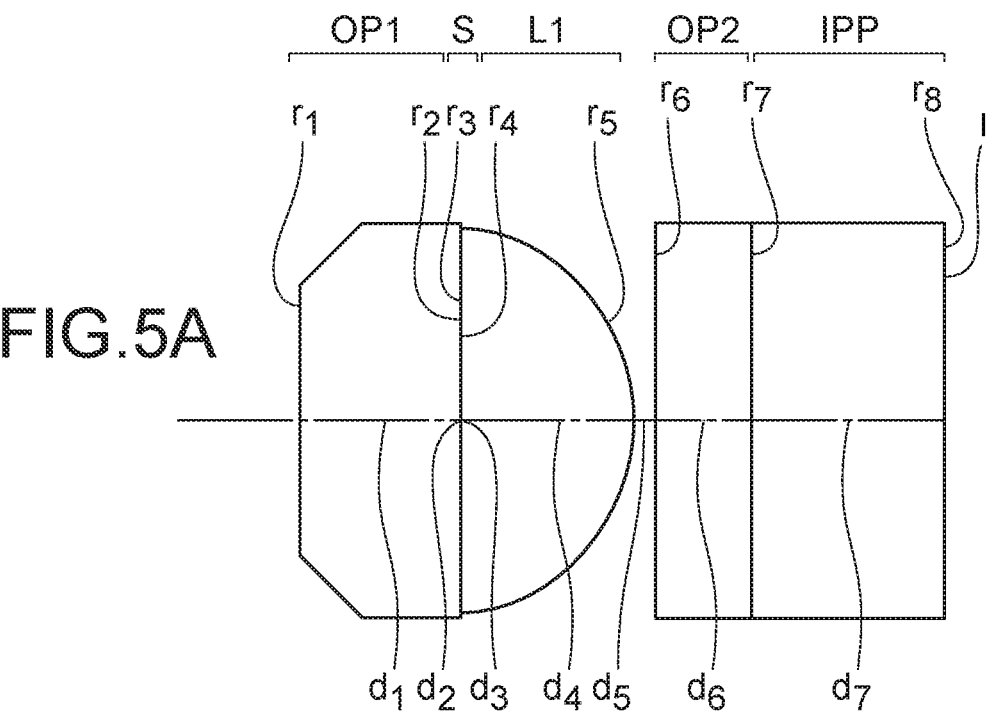
FIG.5A
FIG.5B  FIG.5C  FIG.5D  FIG.5E
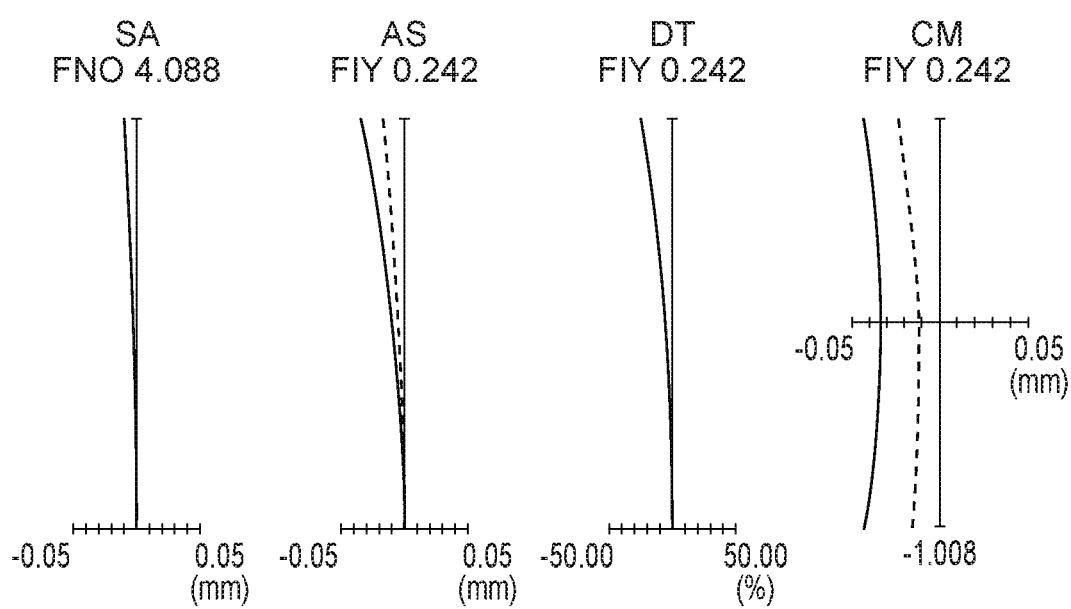

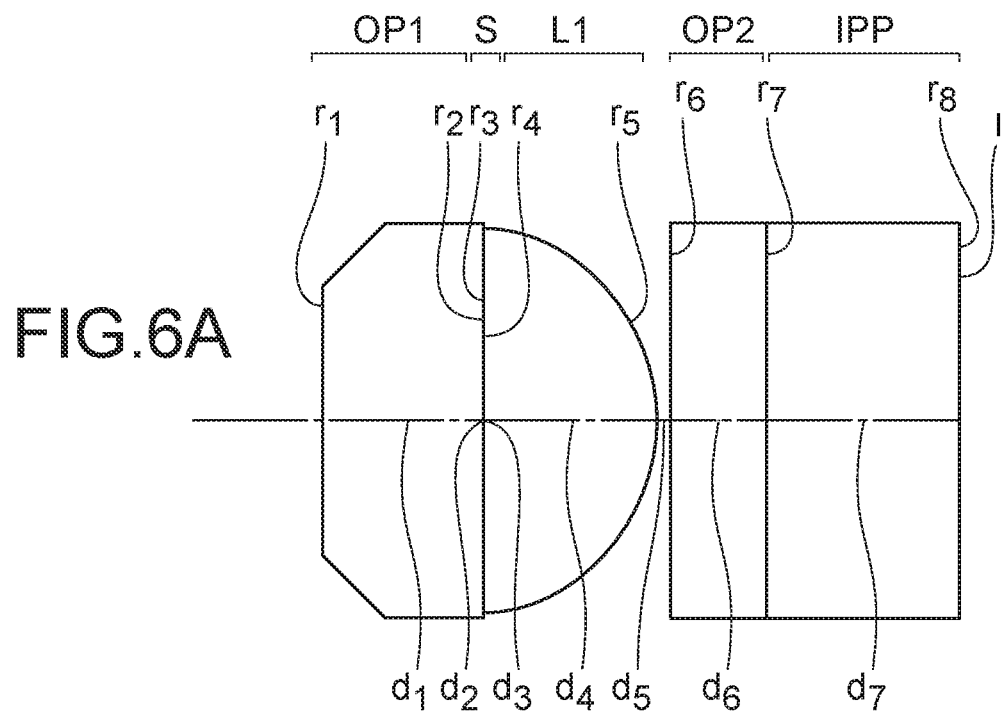
FIG.6A
FIG.6B  FIG.6C  FIG.6D  FIG.6E
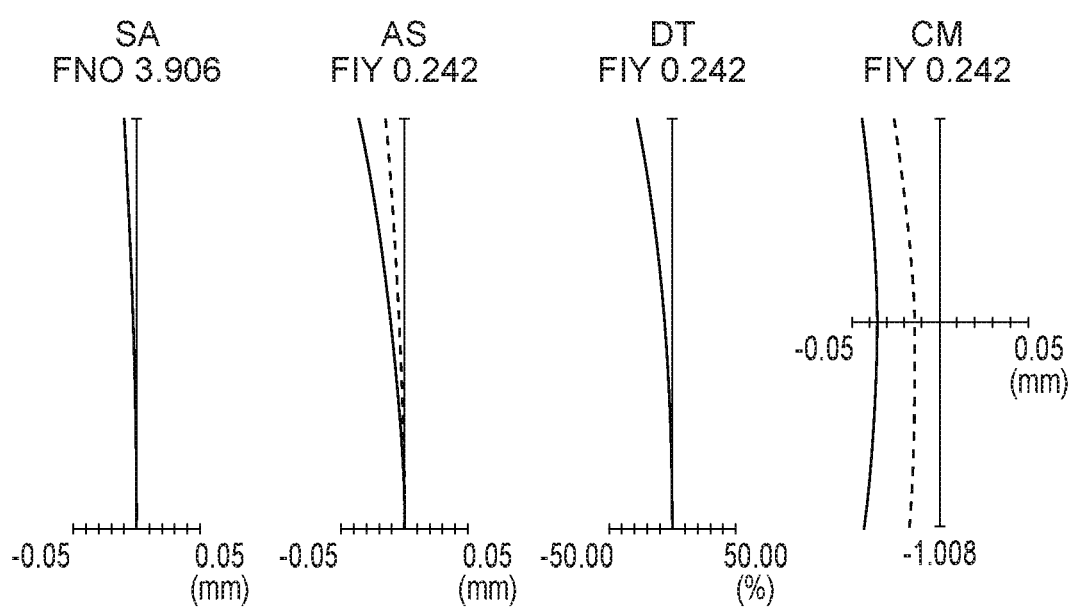

OBJECTIVE OPTICAL SYSTEM, IMAGE PICKUP APPARATUS, AND ENDOSCOPE

CROSS REFERENCES TO RELATED APPLICATION

The present application is a continuation application of PCT/JP2020/006586 filed on Feb. 19, 2020; the entire contents of which are incorporated herein by reference.

BACKGROUND OF INVENTION

Technical Field

The present invention relates to an objective optical system, an image pickup apparatus, and an endoscope.

Description of the Related Art

An ultrasonic endoscope has an operation part and an insert part. The insert part is provided with a transducer and an objective optical system. The transducer is used to pick up ultrasonic images, and the objective optical system is used to pick up optical images.

When operating the ultrasonic endoscope, the operator inserts the insert part into a human body while seeing an optical image. When the distal end of the insert part reaches an object to be observed, the ultrasonic endoscope emits ultrasonic waves to the object to be observed. The object to be observed reflects the ultrasonic waves, and an ultrasonic image is created using the reflected ultrasonic waves.

The operator makes a diagnosis of the observed object or applies a treatment to the observed object while seeing an ultrasonic image. For example, in the case where the observed object is a biomembrane, a diagnosis is made based on an ultrasonic image of a deep portion of the biomembrane. Biopsy may be performed with the biomembrane.

The transducer is generally disposed at the distal end of the insert part. This position of the transducer facilitates contact of the transducer and the observed object or disposition of a balloon between the transducer and the observed object. Since the transducer is disposed at the end of the insert part, the objective optical system is disposed closer to the operation part than the transducer.

Diagnosis or treatment of the observed object is performed based on the ultrasonic image. Therefore, it is important for the ultrasonic endoscope to create ultrasonic images having high image quality. To create ultrasonic images with high image quality, it is helpful that the transducer be disposed in a large space. To provide a large space, it is preferred that the objective optical system be small.

An example of the objective optical system for an endoscope is an endoscope camera lens disclosed in Japanese Patent Application Laid-Open No. 2015-127741. The endoscope camera lens has a lens and a waterproof glass.

SUMMARY OF THE INVENTION

To solve the above problem and to achieve the object, an objective optical system according to some embodiments of the present invention comprises, in order from the object side:
a flat plate;
an aperture stop; and
a substantially hemispherical planoconvex lens having an outer diameter substantially equal to the outer diameter of the flat plate,
wherein the flat plate and the planoconvex lens are cemented together with the aperture stop between, and the objective optical system satisfies the following conditional expressions (1), (2), and (3):

$$0.3 < IH/Dp < 0.45 \tag{1}$$

$$1.7 < 1 + Dp \times \omega r/(2 \times IH) < 2.1 \tag{2}$$

$$0.9 < NL/(1 + Dp \times \omega r/(2 \times IH)) < 1.1 \tag{3}$$

where $\omega r = 2 \times \pi \times |\omega|/360°$, IH is the largest image height, Dp is the outer diameter of the flat plate, $\omega$ is the half angle of view, and NL is the refractive index of the planoconvex lens.

An image pickup apparatus according to some embodiments of the present invention comprises an objective optical system, the objective optical system comprising, in order from the object side:
a flat plate;
an aperture stop; and
a substantially hemispherical planoconvex lens having an outer diameter substantially equal to the outer diameter of the flat plate,
wherein the flat plate and the planoconvex lens are cemented together with the aperture stop between, and the objective optical system satisfies the following conditional expressions (1), (2), and (3):

$$0.3 < IH/Dp < 0.45 \tag{1}$$

$$1.7 < 1 + Dp \times \omega r/(2 \times IH) < 2.1 \tag{2}$$

$$0.9 < NL/(1 + Dp \times \omega r/(2 \times IH)) < 1.1 \tag{3}$$

where $\omega r = 2 \times \pi \times |\omega|/360°$, IH is the largest image height, Dp is the outer diameter of the flat plate, $\omega$ is the half angle of view, and NL is the refractive index of the planoconvex lens.

An endoscope according to some embodiments of the present invention comprises an objective optical system, the objective optical system comprising, in order from the object side:
a flat plate;
an aperture stop; and
a substantially hemispherical planoconvex lens having an outer diameter substantially equal to the outer diameter of the flat plate,
wherein the flat plate and the planoconvex lens are cemented together with the aperture stop between, and the objective optical system satisfies the following conditional expressions (1), (2), and (3):

$$0.3 < IH/Dp < 0.45 \tag{1}$$

$$1.7 < 1 + Dp \times \omega r/(2 \times IH) < 2.1 \tag{2}$$

$$0.9 < NL/(1 + Dp \times \omega r/(2 \times IH)) < 1.1 \tag{3}$$

where $\omega r = 2 \times \pi \times |\omega|/360°$, IH is the largest image height, Dp is the outer diameter of the flat plate, $\omega$ is the half angle of view, and NL is the refractive index of the planoconvex lens.

BRIEF DESCRIPTION OF THE DRAWINGS

FIG. 3A is a cross sectional view of the lenses in an objective optical system of example 1;

FIGS. 3B, 3C, 3D, and 3E are diagrams showing aberrations of the objective optical system of example 1;

FIG. 4A is a cross sectional view of the lenses in an objective optical system of example 2;

FIGS. 4B, 4C, 4D, and 4E are diagrams showing aberrations of the objective optical system of example 2;

FIG. 5A is a cross sectional view of the lenses in an objective optical system of example 3;

FIGS. 5B, 5C, 5D, and 5E are diagrams showing aberrations of the objective optical system of example 3;

FIG. 6A is a cross sectional view of the lenses in an objective optical system of example 4;

FIGS. 6B, 6C, 6D, and 6E are diagrams showing aberrations of the objective optical system of example 4;

DETAILED DESCRIPTION OF THE INVENTION

In the following, embodiments of the objective optical system, the image pickup apparatus, and the endoscope will be described. Specifically, the structures of the embodiments, the reason why such structures are employed, and the operations of the embodiments will be described. It should be understood that the present invention is not limited by the embodiments.

The objective optical system of this embodiment includes, in order from the object side, a flat plate, an aperture stop, and a substantially hemispherical planoconvex lens having an outer diameter substantially equal to the outer diameter of the flat plate. The flat plate and the planoconvex lens are cemented together with the aperture stop between. The objective optical system satisfies the following conditional expressions (1), (2), and (3):

$$0.3 < IH/Dp < 0.45 \quad (1)$$

$$1.7 < 1 + Dp \times \omega r/(2 \times IH) < 2.1 \quad (2)$$

$$0.9 < NL/(1 + Dp \times \omega r/(2 \times IH)) < 1.1 \quad (3)$$

where $\omega r = 2\pi \times |\omega|/360°$, IH is the largest image height, Dp is the outer diameter of the flat plate, $\omega$ is the half angle of view, and NL is the refractive index of the planoconvex lens.

Figure 1A:
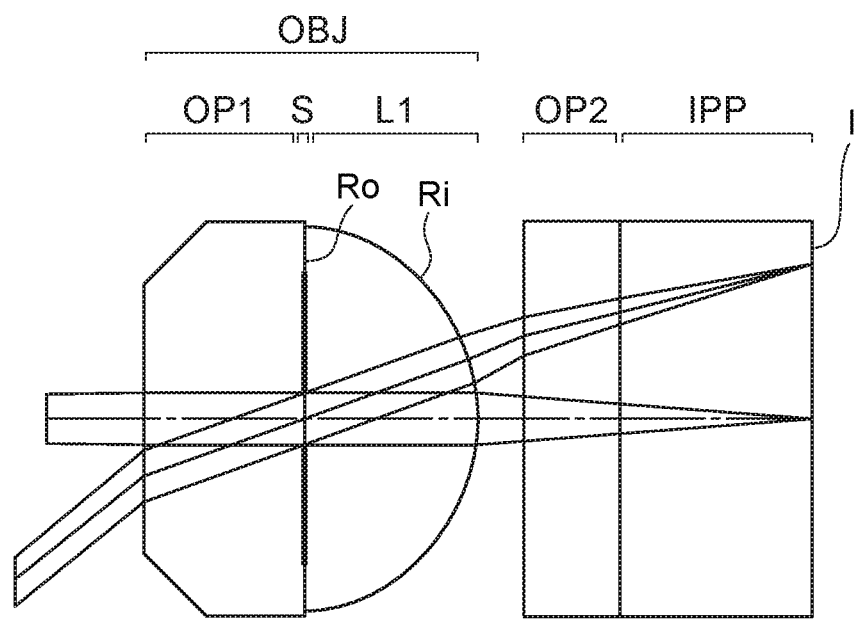
FIGS. 1A and 1B are diagrams showing cross sections of the lenses in objective optical systems according to an embodiment.
Figure 1B:
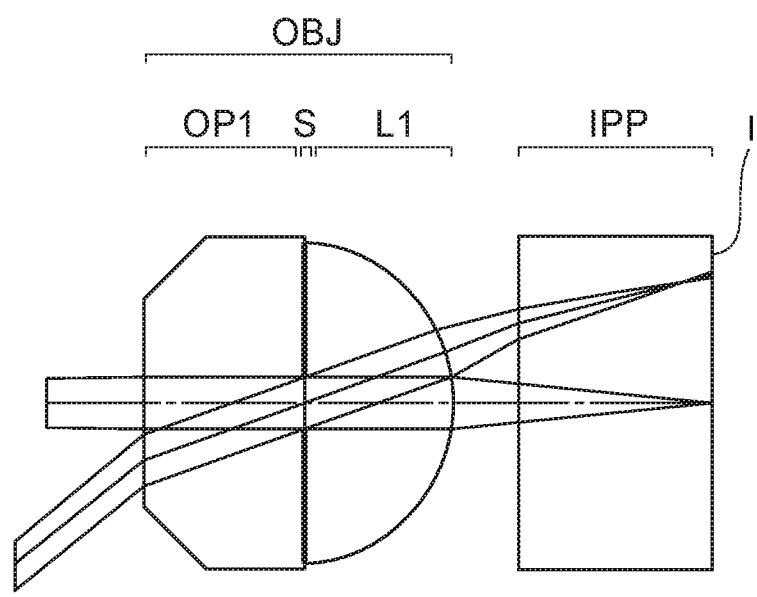

The objective optical system of this embodiment will be specifically described. FIGS. 1A and 1B are diagrams illustrating a cross section of the lenses in exemplary objective optical systems of this embodiment. FIG. 1A is a diagram illustrating a cross section of the lenses in a first exemplary objective optical system. FIG. 1B is a diagram illustrating a cross section of the lenses in a second exemplary objective optical system.

The first exemplary objective optical system. OBJ and the second exemplary objective optical system OBJ include, in order from the object side, a flat plate OP1, an aperture stop S, and a planoconvex lens L1.

The planoconvex lens L1 has an object side surface Ro and an image side surface Ri. The object side surface Ro is a flat surface, and the image side surface Ri is a spherical surface.

In FIGS. 1A and 1B, the light blocking portion of the aperture stop S is drawn by thick lines to facilitate the visibility. In order to indicate the object side surface Ro, the light blocking portion in FIG. 1A is illustrated as if it did not extend to the edge of the object side surface Ro. However, the light blocking portion may extend to the edge of the object side surface Ro as shown in FIG. 1B.

The image side surface of the flat plate OP1 and the object side surface of the planoconvex lens L1 are flat surfaces. The flat plate OP1 and the planoconvex lens L1 are cemented together by the image side surface of the flat plate OP1 and the object side surface of the planoconvex lens L1. They may be cemented using, for example, an optical adhesive.

The aperture stop is located between the image side surface of the flat plate OP1 and the object side surface of the planoconvex lens L1. Thus, the flat plate OP1 and the planoconvex lens L1 are cemented with the aperture stop S between.

The objective optical system OBJ forms an optical image on the image plane I. This optical image can be picked up by an imager. To this end, the image pickup surface of the imager is disposed at the image plane I. In the case where the imager has a flat plate IPP, the flat plate IPP is located between the planoconvex lens L1 and the image plane I. An example of the flat plate IPP is one used for the purpose of sealing the imager.

A flat plate OP2 may additionally be provided between the planoconvex lens L1 and the flat plate IPP, if necessary. The first exemplary system is provided with such a flat plate OP2, as shown in FIG. 1A. The second exemplary system is not provided with such a flat plate OP2, as shown in FIG. 1B. The flat plate OP2 is used to attach of fix the imager to the lens frame.

Among the surfaces of the optical components in the objective optical system OBJ, the object side surface of the flat plate OP1, the image side surface of the flat plate OP1, and the object side surface of the planoconvex lens L1 are flat surfaces, and the image side surface of the planoconvex lens L1 is a surface convex toward the image side. Thus, only the image side surface of the planoconvex lens L1 is an optical surface having a refractive power. In other words, only the planoconvex lens L1 is a lens having a refractive power in the objective optical system OBJ.

The outer diameter of the planoconvex lens L1 is substantially equal to the outer diameter of the flat plate OP1. As will be described later, the objective optical system OBJ is held on the lens frame by the flat plate OP1. To this end, it is preferred that the outer diameter of the planoconvex lens L1 be equal to or smaller than the outer diameter of the flat plate OP1.

Thus, it is possible to hold the flat plate OP1 and the planoconvex lens L1 only by providing a space for holding the flat plate OP1. This can lead to simplification of the structure of the lens frame. Moreover, it is possible to cement the flat plate OP1 and the planoconvex lent L1 together with reference to their outer circumferences.

Shape of Planoconvex Lens L1

The shape of the planoconvex lens L1 in the objective optical system of this embodiment is hemispherical. The hemispherical lens can be produced by grinding a ball lens.

A portion of the ball lens is removed by grinding. Specifically, a planar surface is formed by grinding to produce a lens having a substantially hemispherical shape.

Figure 2A:
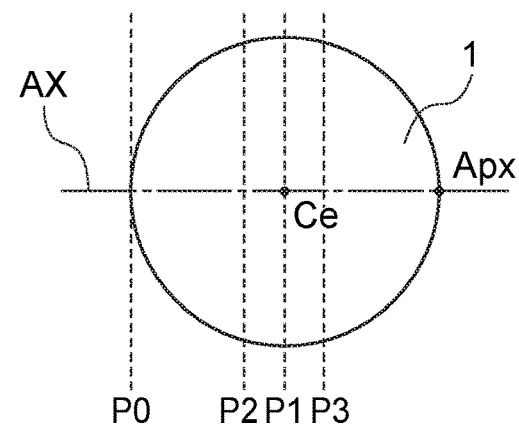
FIGS. 2A, 2B, 2C, and 2D are diagrams illustrating a cross section of a ball lens and cross sections of substantially hemispherical lenses.
Figure 2B:
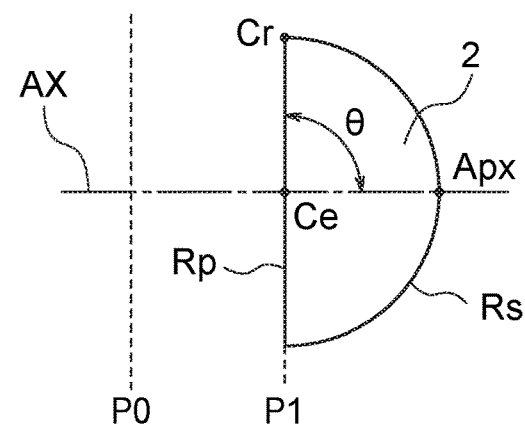
Figure 2C:
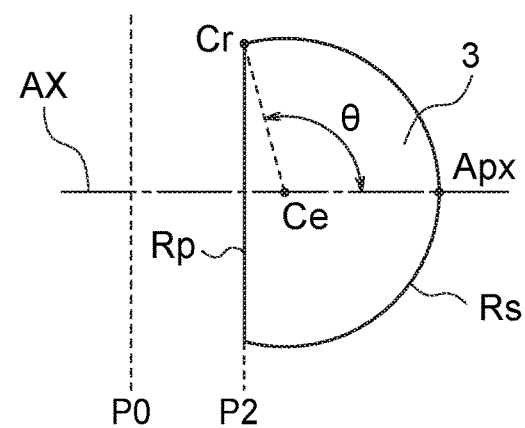
Figure 2D:
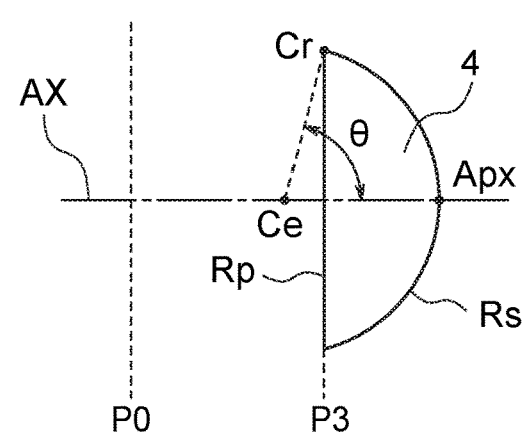
Figure 7A:
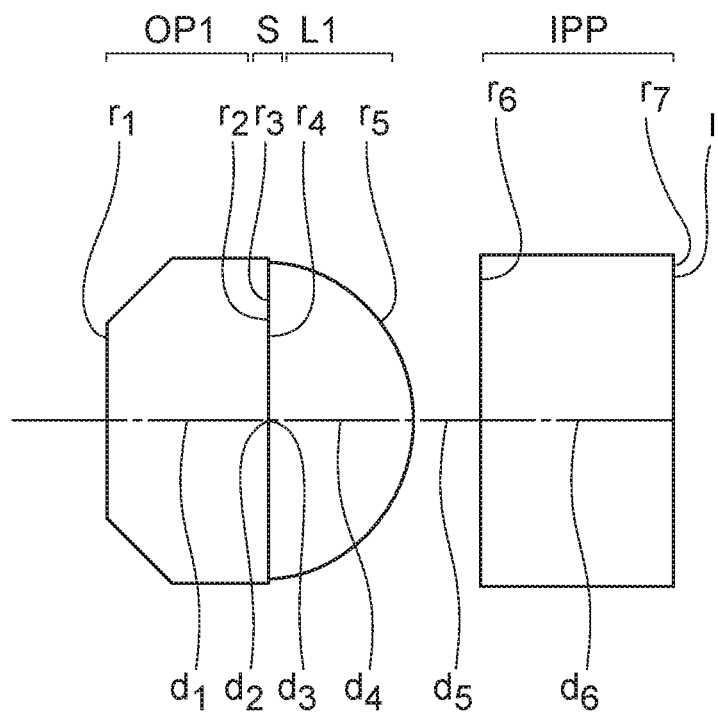
FIG. 7A is a cross sectional view of the lenses in an objective optical system of example 5.
Figures 7B, 7C, 7D, 7E:
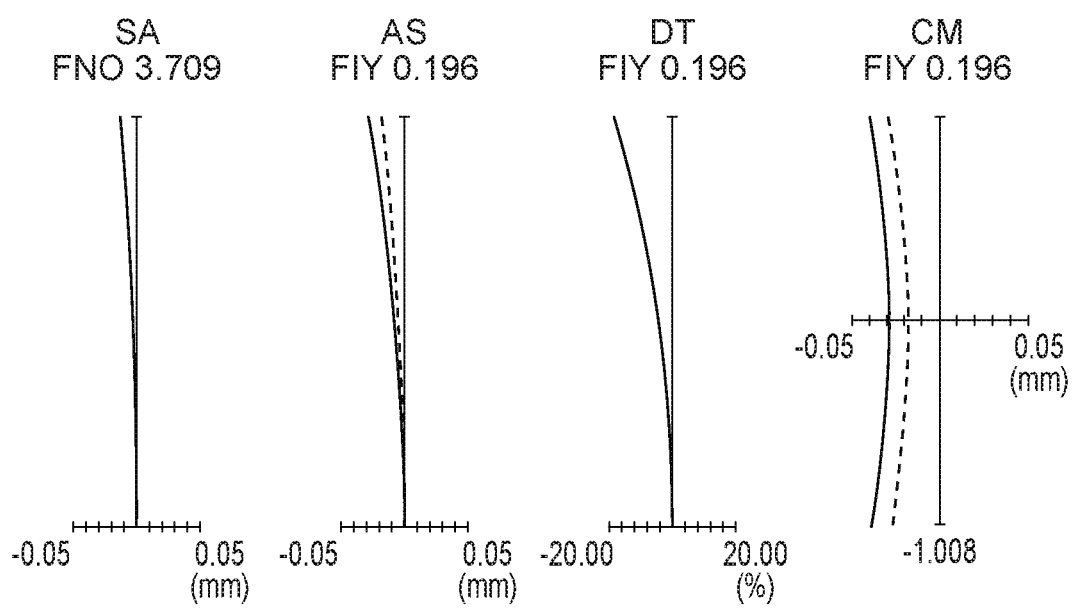
FIGS. 7B, 7C, 7D, and 7E are diagrams showing aberrations of the objective optical system of example 5.

FIGS. 2A, 2B, 2C, and 2D are diagrams illustrating a cross section of a ball lens and cross sections of substantially hemispherical lenses. FIG. 2A is a diagram showing a cross section of the ball lens. FIGS. 2B, 2C, and 2D are diagrams showing cross sections of the substantially hemispherical lenses.

The material of the ball lens 1 is glass. In the process of producing a substantially hemispherical lens using the ball lens 1, the ball lens 1 is ground from its end toward its center.

In FIG. 2A, position P0 is the position at which grinding is started. Grinding proceeds toward the apex Apx. Positions P1, P2, and P3 are the positions at which grinding ends. The range from position P0 to position P1, the range from the position P0 to position P2, and the range from position P0 to position P3 are ranges through which the glass is removed by grinding.

As shown in FIG. 2B, grinding the ball lens 1 from position P0 to position P1 will produce a substantially hemispherical lens 2, which will be simply referred to as "lens 2" hereinafter. The lens 2 has a ground surface Rp and a spherical surface Rs.

Position P1 coincides with the position of the sphere center Ce (i.e. the center of the spherical ball lens 1). In this case, the thickness of the glass removed by grinding (which will be referred to as the thickness Tp hereinafter) is equal to the thickness of the remaining glass (which will be referred to as the thickness Tnp hereinafter).

In this case, the thickness Tnp is equal to the thickness of the hemispherical lens. Hence, the lens 2 is a hemispherical lens.

As shown in FIG. 2C, grinding the ball lens 1 from position P0 to position P2 will produce a substantially hemispherical lens 3, which will be simply referred to as "lens 3" hereinafter. The lens 3 has a ground surface Rp and a spherical surface Rs.

Position P2 does not coincide with position of the sphere center Ce. The distance from position P0 to position P2 is shorter than the distance from position P0 to the sphere center Ce. Thus, the thickness Tp is smaller than the thickness Tnp in this case.

In this case, the thickness Tnp is larger than the thickness of the hemispherical lens. Hence, the lens 3 is thicker than the hemispherical lens.

As shown in FIG. 2D, grinding the ball lens 1 from position P0 to position P3 will produce a substantially hemispherical lens 4, which will be simply referred to as "lens 4" hereinafter. The lens 4 has a ground surface Rp and a spherical surface Rs.

Position P3 does not coincide with position of the sphere center Ce. The distance from position P0 to position P3 is longer than the distance from position P0 to the sphere center Ce. Thus, the thickness Tp is smaller than the thickness Tnp in this case.

In this case, the thickness Tnp is smaller than the thickness of the hemispherical lens. Hence, the lens 4 is thinner than the hemispherical lens.

As above, substantially hemispherical lenses include hemispherical lenses, lenses thicker than hemispherical lenses, and lenses thinner than hemispherical lenses. Therefore, the planoconvex lens L1 is either one of a hemispherical lens, a lens thicker than a hemispherical lens, and a lens thinner than a hemispherical lens.

In the case of the hemispherical lens (i.e. the lens 2) and the lens thicker than the hemispherical lens (i.e. the lens 3), the diameter of the ball lens 1 represents the outer diameter of the substantially hemispherical lens. In the case of the lens thinner than the hemispherical lens (i.e. the lens 4), the diameter of the ground surface Rp represents the outer diameter of the substantially hemispherical lens.

The substantially hemispherical lens is produced by grinding the ball lens 1. In the process of producing the substantially hemispherical lens, centering and edging is not performed. Therefore, the process of producing the substantially hemispherical lens can be made simple. One characterizing feature of the objective optical system of this embodiment is the use of the substantially hemispherical lens, whose production does not require centering and edging.

In the following, conditional expressions (1), (2), and (3) will be described.

Conditional expression (1) defines a condition for achieving an appropriate ratio of the largest image height and the outer diameter of the flat plate. The objective optical system of this embodiment includes only the flat plate and the planoconvex lens. The outer diameter of the objective optical system is defined by the outer diameter of the flat plate or the outer diameter of the planoconvex lens. Since the outer diameter of the planoconvex lens is substantially equal to that of the flat plate, the outer diameter of the flat plate defines the outer diameter of the objective optical system. Conditional expression (1) may be considered to be a conditional expression used to determine an appropriate ratio of the largest image height and the outer diameter of the objective optical system.

As shown in FIG. 1A, while the edge of the non-cemented surface of the flat plate OP1 is chamfered, the edge of its cemented surface is not chamfered. Hence, the outer diameter of the flat plate OP1 differs between the non-cemented surface side and the cemented surface side. In this case, the largest outer diameter of the flat plate may be regarded as the parameter Dp.

If the value of IH/Dp falls below the lower limit of conditional expression (1), the outer diameter of the flat plate is too large in relation to the largest image height. This will make the objective optical system bulky.

The objective optical system of this embodiment can be used as the objective optical system of an endoscope. In that case, the objective optical system is provided in the insert part of the endoscope. The bulkiness of objective optical system is obstructive for downsizing of the diameter of the insert part. For this reason, falling below the lower limit of conditional expression (1) is undesirable.

If the value of IH/Dp exceeds the upper limit of conditional expression (1), the outer diameter of the flat plate is too small in relation to the largest image height. This will make the size of the objective optical system unnecessarily small.

The optical image formed by the objective optical system can be picked up by the imager. In this connection, the largest image height may be regarded as the size of the image pickup surface of the imager. As described above, the outer diameter of the flat plate defines the outer diameter of the objective optical system. Therefore, if the outer diameter of the flat plate is too small in relation to the largest image height, the outer diameter of the objective optical system is unduly small in relation to the size of the imager. In other words, the objective optical system is downsized more than necessary.

In cases where the objective optical system of this embodiment is used as the objective optical system of an endoscope, the objective optical system and the imager are disposed in the insert part of the endoscope. If the outer diameter of the objective optical system is small in relation to the size of the imager, the thickness of the insert part is affected by the size of the imager but not affected by the outer diameter of the objective optical system. Then, it is not necessary to downsize the objective optical system unnecessarily.

The larger the outer diameter of the objective optical system is, the easier the production (or manufacturing) of the objective optical system is. Easy production can lead to reduction in the production cost. Hence, downsizing the objective optical system unnecessarily leads to increases in the difficulty and the cost of production. For this reason, exceeding the upper limit of conditional expression (1) is undesirable.

Conditional expression (2) relates to the estimated refractive index of the planoconvex lens.

Among the optical elements in the objective optical system of this embodiment, only the planoconvex lens has a refractive power. The refractive index of the planoconvex lens in the objective optical system of this embodiment depends on other parameters, and the degree of flexibility in designing the refractive index is low.

A first limitation leading to the above dependency is that the focal length of the planoconvex lens depends on the angle of view 2ω and the largest image height IH. A second limitation leading to the above dependency is that the radius of curvature of the convex surface of the planoconvex lens is approximately half the outer diameter Dp of the flat plate.

Due to the above limitations, the refractive index of the planoconvex lens is dependent on the outer diameter Dp of the flat plate, the half angle of view ω, and the largest image height IH. An equation that these four parameters would satisfy was formulated based on a hypothesis. The value of "1+Dp×ωr/(2×IH)" in conditional expression (2) represents the refractive index derived from this equation. This value will be referred to as the estimated refractive index.

The glass of the planoconvex lens must be selected from glass materials having refractive indices close to the estimated refractive index. Therefore, it is necessary to determine relationship between the half angle of view ω, the largest image height IH, and the outer diameter Dp of the flat plate in such a way that the estimated refractive index falls in an appropriate range. How conditional expression (2) is derived will be specifically described later.

If the value of "1+Dp×ωr/(2×IH)" in conditional expression (2) falls below the lower limit of conditional expression (2), the refractive index of glass materials that can be used for the planoconvex lens is unduly low. The unduly low refractive index of glass materials leads to increased spherical aberration and coma. Therefore, falling below the lower limit of conditional expression (2) is undesirable.

If the value "1+Dp×ωr/(2×IH)" in conditional expression (2) exceeds the upper limit of conditional expression (2), the refractive index of glass materials that can be used for the planoconvex lens is unduly high. If the required refractive index of glass is unduly high, for example, multicomponent glass having a high refractive index should be selected for the planoconvex lens. Multicomponent glass having a high refractive index shows ultra-high dispersion, leading to increased chromatic aberration.

A crystal may be used as the material of the planoconvex lens. However, crystals having a high refractive index generally shows birefringence. Therefore, use of a crystal for the planoconvex lens leads to blurred images.

As above, whether a multicomponent glass material or a crystal is selected as the material of the planoconvex lens, deteriorated imaging performance will result. For this reason, exceeding the upper limit of conditional expression (2) is undesirable.

The variety of glass materials that can be used for lenses is not unlimited. If the required refractive index is too high, there are no glass material that can be used for the planoconvex lens.

Conditional expression (3) is a condition for limiting the refractive index of the planoconvex lens appropriately. If the value of NL/(1+Dp×ωr/(2×IH)) in conditional expression (3) is close to 1, it means that an appropriate glass material having a refractive index close to the estimated refractive index is selected as the glass material of the planoconvex lens.

If the value of NL/(1+Dp×ωr/(2×IH)) in conditional expression (3) falls below the lower limit, the refractive index NL of the planoconvex lens is too low in relation to the estimated refractive index. The refractive index NL lower than the estimated refractive index means deficient refractive power of the planoconvex lens. Then, in order to achieve a desired focal length and a desired angle of view, it is necessary to increase the deficient refractive power of the planoconvex lens by other parameters.

To increase the refractive power of the planoconvex lens, the radius of curvature of the convex surface may be decreased. However, decreasing the radius of curvature of the convex surface leads to a decrease in the outer diameter of the planoconvex lens. The difference in the outer diameter between the flat plate and the planoconvex lens smaller than the flat plate tends to cause decentering in cementing the planoconvex lens and the flat plate. This will make the cementing of the planoconvex lens and the flat plate unsatisfactory. For this reason, falling below the lower limit of conditional expression (3) is undesirable.

If the value of NL/(1+Dp×ωr/(2×IH)) in conditional expression (3) exceeds the upper limit, the refractive index of the planoconvex lens is too high. The refractive index NL higher than the estimated refractive index means excessive refractive power of the planoconvex lens. Then, in order to achieve a desired focal length and a desired angle of view, it is necessary to decrease the excessive refractive power of the planoconvex lens by other parameters.

To decrease the refractive power of the planoconvex lens, the radius of curvature of the convex surface may be increased. However, increasing the radius of curvature of the convex surface leads to an increase in the outer diameter of the planoconvex lens.

The lens frame is basically designed to have an inner diameter matched with the outer diameter of the flat plate. Hence, if the outer diameter of the planoconvex lens is larger than the outer diameter of the flat plate, the planoconvex lens cannot be housed in the lens frame.

To house the planoconvex lens in the lens frame, the outer diameter of the planoconvex lens may be made equal to the outer diameter of the flat plate. To make the outer diameter of the planoconvex lens equal to the outer diameter of the flat plate, centering and edging may be applied to the planoconvex lens. However, applying centering and edging to the planoconvex lens is contradictory to the initial intention of using a substantially hemispherical lens, for which centering and edging is not necessary.

To house the planoconvex lens in the lens frame, the inner diameter of the lens frame may be increased to match with the outer diameter of the planoconvex lens. However, increasing the inner diameter of the lens frame leads to an increase in the size of the lens frame. For this reason, exceeding the upper limit of conditional expression (3) is undesirable.

It is preferred that the objective optical system satisfy the following conditional expressions (4) and (5):

$$1.7 < Np \quad (4)$$

$$0.3 < Tp/Dp < 0.7 \quad (5)$$

where Np is the refractive index of the flat plate, Tp is the thickness of the flat plate on the optical axis, and Dp is the outer diameter of the flat plate.

Conditional expression (4) defines the refractive index of the flat plate.

The flat plate has two optical surfaces. In the process of producing the flat plate, burrs are sometimes formed on its outer circumference. The burrs on the outer circumference of the flat plate may form indentations in the peripheral or outer portion of the optical surfaces. When light passes through such indentations, light is diffused. This may cause flare.

If the distance from the circumference to the position of passing rays is large, indentations will not be formed in the range in which rays pass, even if there are burrs on the outer circumference. This makes the tolerable level for burrs high.

If the value of Np in conditional expression (4) falls below the lower limit, the refractive index of the flat plate is too low. Then, the height of rays incident on the flat plate is high. When the ray height is high, the position of passing rays is close to the outer circumference of the flat plate. In other words, the distance between the outer circumference and the position of passing rays is short. This makes the tolerable level for burrs low.

The objective optical system is held in the lens frame by the flat plate. When the flat plate is attached or adhered to the lens frame, excess adhesive may extend on the flat plate. Such excess adhesive may form projections in the peripheral or outer portion of the flat plate. When light passes through such projections, light is diffused. This may cause flare.

If the distance from the circumference to the position of passing rays is large, projection will not be formed in the range in which rays pass, even if there is excess adhesive. This makes the tolerable level for excess adhesive high.

If the distance from the circumference to the position of passing rays is short, the tolerable level for excess adhesive becomes low. For this reason, falling below the lower limit of conditional expression (4) is undesirable.

Conditional expression (5) defines a condition for making the ratio of the thickness of the flat plate on the optical axis and the largest outer diameter of the flat plate appropriate.

If the value of Tp/Dp in conditional expression (5) falls below the lower limit, the thickness of the flat plate on the optical axis is too small. The objective optical system is held in the lens frame by the flat plate. If the thickness of the flat plate on the optical axis is too small, the area of contact between the outer circumferential surface of the flat plate and the lens frame may be insufficient. Then, it will be difficult to hold the objective optical system by the lens frame stably. For this reason, falling below the lower limit of conditional expression (5) is undesirable.

If the value of Tp/Dp in conditional expression (5) exceeds the upper limit, the thickness of the flat plate on the optical axis is too large. Then, the height of rays incident on the flat plate is high. When the height of rays is high, the rays are close to the outer circumference of the flat plate. In consequence, the margin of the ray height in relation to the outer circumference is small.

The small margin of the ray height in relation to the outer circumference makes the tolerable level for burrs low. Moreover, it also makes the tolerable level for excess adhesive low. For this reason, exceeding the upper limit of conditional expression (5) is undesirable.

The aperture stop in the objective optical system of this embodiment has a light transmitting portion and a light blocking portion. It is preferred that the light blocking portion be constituted by a light blocking film.

The aperture stop has the light transmitting portion and the light blocking portion. The light transmitting portion constitutes the aperture of the aperture stop. The light blocking portion may be formed using a light blocking film. With the use of a light blocking film, the light blocking portion can be formed with high precision.

The light blocking portion using a light blocking film can be formed by, for example, chrome deposition and photo etching. Chrome may be replaced by other deposition materials.

It is possible by chrome deposition to form an aperture having a diameter equal to or smaller than 0.1 mm. Hence, it is possible to easily produce an aperture stop having a very small aperture.

A thin metal plate may be used as the aperture stop. The light blocking portion may be formed by an optical multilayer film or application of a light blocking paint.

It is preferred that the aperture stop in the objective optical system of this embodiment be provided on the image side surface of the flat plate or the object side surface of the planoconvex lens.

In the case where the aperture stop is provided on the flat plate, it is necessary to perform centering and edging to align the center of the outer diameter of the flat plate and the center of the aperture. Even if the outer diameter of the flat plate is as small as 0.5 mm, it is possible to perform centering and edging.

The surface on which the aperture stop is formed may be either the image side surface of the flat plate or the object side surface of the planoconvex lens. In any case, in order to form the light blocking portion with high precision, it is necessary that the surface on which the aperture stop is to be formed be held stably.

The flat plate has an outer circumferential surface extending between the object side surface and the image side surface. The circumferential surface partly has a shape of the side surface of a cylinder. In contrast, the planoconvex lens does not have an outer circumferential surface between the object side surface and the image side surface.

In the case where an element is held by its outer circumferential surface, stable holding can be achieved with a simple holding structure. As above, while the flat plate has an outer circumferential surface, the planoconvex lens does not have an outer circumferential surface. Therefore, it is preferred that the aperture stop be formed on the image side surface of the flat plate.

A preferred shape of the substantially hemispherical lens (or planoconvex lens) will now be described.

The planoconvex lens in the objective optical system of this embodiment has a flat surface and a spherical surface. It is preferred that the edge of the flat surface and the edge of the spherical surface join directly.

As shown in FIG. 1A, the planoconvex lens L1 has an object side surface Ro and an image side surface Ri. The object side surface Ro is a flat surface. The image side surface Ri is a spherical surface. The edge of the object side surface Ro of the planoconvex lens L1 and the edge of the image side surface Ri thereof join directly.

As shown in FIGS. 2B, 2C, and 2D, lens 2, lens 3, and lens 4 each has a ground surface Rp and a spherical surface Rs. The ground surface Rp is a flat surface. The spherical surface Rs is a part of the sphere of the ball lens 1. The edge of the ground surface Rp and the edge of the spherical surface Rs of each of lenses 2, 3, and 4 join directly.

Each of lenses 2, 3, and 4 is produced by grinding the ball lens 1. Thus, the planoconvex lens L1 may also be produced by grinding a ball lens. The planoconvex lens L1 having the object side surface Ro and the image side surface Ri edges of which join directly can be produced by grinding the ball lens 1.

It is preferred that the objective optical system of this embodiment satisfy the following conditional expression (6):

$$75° \leq \theta \leq 105° \quad (6),$$

where θ is the magnitude of the angle formed by the optical axis and the straight line connecting a point on the outer circumference of the object side surface of the planoconvex lens and the center of curvature of the image side surface.

In FIGS. 2B, 2C, and 2D respectively showing lenses 2, 3, and 4, the magnitude of the angle formed by the optical axis and the straight line connecting a point on the outer circumference of the object side surface of the planoconvex lens and the center of curvature of the image side surface is represented by θ. This magnitude will be referred to as the specific magnitude of angle. The specific magnitude of angle is the magnitude of a specific angle. The specific angle is the angle formed by the straight line connecting the intersection point Cr and the sphere center Ce and the optical axis AX.

The intersection point Cr is a point on the outer circumference of the ground surface Rp. The edge of the ground surface Rp and the edge of the spherical surface Rs join directly. Therefore, the intersection point Cr is a point on the outer circumference of the spherical surface Rs also.

In the case of lens 2, the specific angle is the right angle. Hence, lens 2 is a hemispherical lens. In the case of lens 3, the specific angle is an obtuse angle. Hence, lens 3 is a lens thicker than the hemispherical lens. In the case of lens 4, the specific angle is an acute angle. Hence, lens 4 is a lens thinner than the hemispherical lens.

As above, the shapes of lens 2, lens 3, and lens 4 can be expressed by the specific angle. Lens 2, lens 3, and lens 4 are substantially hemispherical lenses. Thus, the shapes of substantially hemispherical lenses can be expressed by the specific angle.

The planoconvex lens L1 shown in FIG. 1A is also a hemispherical lens. The shape of the planoconvex lens L1 is also expressed by the specific angle.

The intersection point Cr is a point on the outer circumference of the ground surface Rp. The object side surface Ro of the planoconvex lens L1 corresponds to the ground surface Rp. Therefore, a point on the outer circumference of the object side surface Ro may be used in place of the intersection point Cr.

The sphere center Ce is the center of curvature of the image side surface Ri. The image side surface Ri of the planoconvex lens L1 corresponds to the spherical surface Rs. Therefore, the center of curvature of the image side surface Ri may be used in place of the sphere center Ce.

In consequence, the specific angle of the planoconvex lens L1 is represented by the angle formed by the straight line connecting a point on the outer circumference of the object side surface Ro and the center of curvature of the image side surface Ri and the optical axis AX. Consequently, the magnitude of the angle formed by the straight line connecting a point on the outer circumference of the object side surface Ro and the center of curvature of the image side surface Ri and the optical axis AX is the specific magnitude of angle.

Conditional expression (6) defines the shape of the planoconvex lens.

If θ=90°, the shape of the planoconvex lens is a hemisphere. In that case, the center of curvature of the convex surface of the planoconvex lens coincides with the position of the aperture stop. Then, coma and astigmatism do not occur.

The more the shape of the planoconvex lens deviates from the hemisphere, the larger the positional discrepancy between the center of curvature of the convex surface and aperture stop is, and the larger coma and astigmatism will be.

If conditional expression (6) is satisfied, the deviation of the shape of the planoconvex lens from the hemisphere can be kept small. Then, coma and astigmatism can be kept small. Moreover, increases in the entire length of the optical system and deterioration of the imaging performance due to eccentricity can be controlled.

If the value of θ in conditional expression (6) falls below the lower limit, the deviation of the shape of the planoconvex lens from the hemisphere is too large. Specifically, the thickness of the planoconvex lens is too thin as compared to the thickness of the hemispherical lens. Then, the entire length of the optical system can be kept short. However, the positional discrepancy between the center of curvature of the convex surface and the position of the aperture stop is large. Consequently, large coma and astigmatism will occur.

Moreover, if the value of θ in conditional expression (6) falls below the lower limit, the outer diameter of the planoconvex lens is larger than the diameter of the sphere. Then, the planoconvex lens is prone to be eccentric relative to the flat plate. In the case where the objective lens is held in the lens frame by the flat plate, the eccentricity of the planoconvex lens relative to the flat plate means eccentricity of the planoconvex lens relative to the center axis of the lens frame. This results in deterioration in the imaging performance. For this reason, falling below the lower limit of conditional expression (6) is undesirable.

If the value of θ in conditional expression (6) exceeds the upper limit, the deviation of the shape of the planoconvex lens from the hemisphere is too large. Specifically, the thickness of the planoconvex lens is thicker than the thickness of the hemispherical lens. In this case, the outer diameter of the planoconvex lens is equal to the diameter of the sphere, and there is not variation in diameters among the components.

However, there is a large positional discrepancy between the center of curvature of the spherical surface and the position of the aperture stop. Then, large coma and astigmatism will occur. Moreover, the entire length of the optical system will increase. For this reason, exceeding the upper limit of conditional expression (6) is undesirable.

The planoconvex lens is produced by grinding a ball lens. In the process of grinding, machining errors cause variations in the position of the ground surface Rp. In consequence, the conditional expression (6) is not satisfied in some cases. However, the machining errors are extremely small. Therefore, in cases where the conditional expression (6) is not satisfied due to machining errors, it is considered that conditional expression (6) is satisfied.

It is preferred that the F-number of the objective optical system of this embodiment be equal to or larger than 3.5.

The planoconvex lens is a substantially hemispherical lens. The aperture stop is provided on the object side surface of the planoconvex lens. The center of curvature of the convex surface is located at or near the location of the aperture stop. In consequence, refraction of the principal rays is small on the image side surface of the planoconvex lens. Therefore, astigmatism and coma do not occur, or even if they occur, the amount thereof is small.

In terms of aberrations other than astigmatism and coma, it is preferred that the amount of spherical aberration be small. F-numbers equal to or larger than 3.5 can keep the amount of spherical aberration within an allowable range. In consequence, the objective optical system can form optical images that can be observed without difficulties.

An image pickup apparatus according to this embodiment includes an objective optical system including, in order from the object side, a flat plate, an aperture stop, and a substantially-hemispherical planoconvex lens having an outer diameter substantially equal to the outer diameter of the flat plate. The flat plate and the planoconvex lens are cemented together with the aperture stop between. The objective optical system satisfies the aforementioned conditional expressions (1), (2), and (3).

An endoscope according to this embodiment includes an objective optical system including, in order from the object side, a flat plate, an aperture stop, and a substantially-hemispherical planoconvex lens having an outer diameter substantially equal to the outer diameter of the flat plate. The flat plate and the planoconvex lens are cemented together with the aperture stop between. The objective optical system satisfies the aforementioned conditional expressions (1), (2), and (3).

The objective optical system of this embodiment can form optical images that can be observed without difficulties. In consequence, the image pickup apparatus of this embodiment can pick up images having image qualities that do not lead to difficulties in observing them. In other words, the image pickup apparatus or endoscope can pick up images having image qualities that do not lead to difficulties in observing them.

In the following, examples of the objective optical system will be described specifically with reference to the drawings. It should be understood that the present invention is not limited by the examples.

FIGS. 3A, 4A, 5A, 6A, and 7A are diagrams showing cross sections of the lenses in the examples of the objective optical system. The image plane is denoted as "I" in these drawings.

Drawings include aberration diagrams of the examples of the objective optical system. Specifically, FIGS. 3B, 4B, 5B, 6B, and 7B show spherical aberration (SA), FIGS. 3C, 4C, 5C, 6C, and 7C show astigmatism (AS), FIGS. 3D, 4D, 5D, 6D, and 7D show distortion (DT), and FIGS. 3E, 4E, 5E, 6E, and 7E show coma (CM).

The horizontal axes of each of the aberration diagrams represents the amount of aberration. The unit of aberration is millimeters in spherical aberration, astigmatism, and coma. Distortion is represented by "%". In the aberration diagrams FIY represents the image height in millimeters, and FNO. is the F-number. The unit of wave lengths in aberration diagrams is nanometers.

The objective optical system of example 1 includes a flat plate OP1 and a planoconvex lens L1 arranged in order from the object side. The objective optical system of example 1 also has an aperture stop S provided between the flat plate OP1 and the planoconvex lens L1. The objective optical system of example 1 further has a flat plate OP2 and a flat plate IPP arranged on the image side of the planoconvex lens L1.

The glass material selected for the planoconvex lens L1 of the objective optical system of example 1 was a glass having a refractive index of 1.85646. This resulted in an angle of view substantially equal to a designed angle of view. Specifically, while the designed angle of view was 80°, the angle of view achieved was 79.11°.

The objective optical system of example 2 includes a flat plate OP1 and a planoconvex lens L1 arranged in order from the object side. The objective optical system of example 1 also has an aperture stop S provided between the flat plate OP1 and the planoconvex lens L1. The objective optical system of example 2 further has a flat plate OP2 and a flat plate IPP arranged on the image side of the planoconvex lens L1.

The glass material selected for the planoconvex lens L1 of the objective optical system of example 2 was a glass having a refractive index of 1.91137. This resulted in an angle of view substantially equal to a designed angle of view. Specifically, while the designed angle of view was 85°, the angle of view achieved was 84.75°.

The objective optical system of example 3 includes a flat plate OP1 and a planoconvex lens L1 arranged in order from the object side. The objective optical system of example 1 also has an aperture stop S provided between the flat plate OP1 and the planoconvex lens L1. The objective optical system of example 3 further has a flat plate OP2 and a flat plate IPP arranged on the image side of the planoconvex lens L1.

The glass material selected for the planoconvex lens L1 of the objective optical system of example 3 was a glass having a refractive index of 1.96073. This resulted in an angle of view substantially equal to a designed angle of view. Specifically, while the designed angle of view was 90°, the angle of view achieved was 90.77°.

The objective optical system of example 4 includes a flat plate OP1 and a planoconvex lens L1 arranged in order from the object side. The objective optical system of example 1 also has an aperture stop S provided between the flat plate OP1 and the planoconvex lens L1. The objective optical system of example 4 further has a flat plate OP2 and a flat plate IPP arranged on the image side of the planoconvex lens L1.

The glass material selected for the planoconvex lens L1 of the objective optical system of example 4 was a glass having a refractive index of 2.00912. This resulted in an angle of view substantially equal to a designed angle of view. Specifically, while the designed angle of view was 95°, the angle of view achieved was 95.97°.

The objective optical system of example 5 includes a flat plate OP1 and a planoconvex lens L1 arranged in order from the object side. The objective optical system of example 5 also has an aperture stop S provided between the flat plate OP1 and the planoconvex lens L1. The objective optical system of example 5 further has a flat plate IPP arranged on the image side of the planoconvex lens L1.

The glass material selected for the planoconvex lens L1 of the objective optical system of example 5 was a glass having a refractive index of 1.88815. This resulted in an angle of view substantially equal to a designed angle of view. Specifically, while the designed angle of view was 80°, the angle of view achieved was 79°.

The dimensions of the entire length of the optical system, the outer diameter of the flat plate, the outer diameter of the lens frame, the largest image height, and the angle of view of the optical system in the respective examples are shown in Table 1 below.

TABLE 1

| | ENTIRE LENGTH | FLAT PLATE | OUTER DIAMETER LENS FRAME | LARGEST IMAGE HEIGHT | ANGLE OF VIEW |
|---|---|---|---|---|---|
| EXAMPLE 1 | 1.04 | 0.62 | 0.82 | 0.242 | 79.11 |
| EXAMPLE 2 | 1.02 | 0.62 | 0.82 | 0.242 | 84.75 |
| EXAMPLE 3 | 1.00 | 0.62 | 0.82 | 0.242 | 90.77 |
| EXAMPLE 4 | 0.99 | 0.62 | 0.82 | 0.242 | 95.37 |
| EXAMPLE 5 | 0.88 | 0.52 | 0.72 | 0.196 | 79.00 |

The lens frame is a cylinder having a thickness of 0.1 mm, which is produced by cutting stainless steel. The objective optical system is set inside the lens frame. The variations in the angle of view of the objective optical systems among the examples are achieved by variations in the refractive index of their planoconvex lenses.

The objective optical system of each example may be used as, for example, the objective optical system of an ultrasonic endoscope. It is important for the ultrasonic endoscope to obtain ultrasonic images with high image quality. To achieve this, it is of high priority in the ultrasonic endoscope to provide an enough space in which a transducer is disposed.

The size of the space required to provide each example of the objective optical system disclosed here is equal to a cube having an edge length of approximately 1 mm. Therefore, the size of the space in which the objective optical system is provided can be made very small. In consequence, it is possible to provide a large space for providing a transducer.

In cases where the objective optical system is used in a bronchial ultrasonic endoscope, it is particularly desired that the space in which the objective optical system is provided be small. The examples of objective optical system disclosed here can be used as objective optical systems of bronchial ultrasonic endoscopes.

The angles of view of the objective optical systems of the examples 1 to 5 are smaller than 100°. The angles of view of them are not large as compared to objective optical systems of endoscopes for colon inspection. However, the objective optical systems of the examples 1 to 5 can form optical images that can be observed without difficulties. This enables the operator of the endoscope to see the direction of move of the insert part and the site toward which ultrasonic waves are emitted. In consequence, the operator can operate the ultrasonic endoscope without troubles.

In the following, numeral data of the aforementioned examples will be given. In the surface data, r is the radius of curvature of each surface, d is the distance between adjacent surfaces, ne is the refractive index of each lens at e-line, and νd is the Abbe number of each lens at e-line.

In various date, D0 denotes the object distance, f denotes the focal length of the objective optical system at e-line, FNO. denotes the F-number, IH denotes the largest image height, ω denotes the half angle of view, Lt denotes the entire length of the objective optical system, and Dp denotes the outer diameter of the flat plate. The stops in all the examples are aperture stops. The unit of the numerical values of D0, f, IH, Lt, and Dp is millimeters, and the unit of ω is degrees.

Example 1

Unit mm

| Surface no. | r | d | ne | νe |
|---|---|---|---|---|
| Surface data | | | | |
| 1 | ∞ | 0.25 | 1.88815 | 40.52 |
| 2 | ∞ | 0.00 | | |
| 3 (Stop) | ∞ | 0.00 | | |
| 4 | ∞ | 0.27 | 1.85646 | 40.53 |
| 5 | −0.305 | 0.07 | | |
| 6 | ∞ | 0.15 | 1.51825 | 63.93 |
| 7 | ∞ | 0.30 | 1.51825 | 63.93 |
| 8 | ∞ | 0.00 | | |
| Image plane | ∞ | | | |
| Various data | | | | |
| D0 | | 6 | | |
| f | | 0.356 | | |
| FNO. | | 4.61 | | |
| IH | | 0.242 | | |
| 2ω | | 79.11 | | |
| Lt | | 1.04 | | |
| Dp | | 0.62 | | |

Example 2

Unit mm

| Surface no. | r | d | ne | νe |
|---|---|---|---|---|
| Surface data | | | | |
| 1 | ∞ | 0.25 | 1.88815 | 40.52 |
| 2 | ∞ | 0.00 | | |
| 3 (Stop) | ∞ | 0.00 | | |
| 4 | ∞ | 0.27 | 1.91137 | 34.79 |
| 5 | −0.305 | 0.05 | | |
| 6 | ∞ | 0.15 | 1.51825 | 63.93 |
| 7 | ∞ | 0.30 | 1.51825 | 63.93 |
| 8 | ∞ | 0.00 | | |
| Image plane | ∞ | | | |
| Various data | | | | |
| D0 | | 6 | | |
| f | | 0.335 | | |
| FNO. | | 4.32 | | |
| IH | | 0.242 | | |
| 2ω | | 84.75 | | |
| Lt | | 1.02 | | |
| Dp | | 0.62 | | |

Example 3

Unit mm

| Surface no. | r | d | ne | νe |
|---|---|---|---|---|
| Surface data | | | | |
| 1 | ∞ | 0.25 | 1.88815 | 40.52 |
| 2 | ∞ | 0.00 | | |
| 3 (Stop) | ∞ | 0.00 | | |
| 4 | ∞ | 0.27 | 1.96073 | 32.09 |
| 5 | −0.305 | 0.03 | | |
| 6 | ∞ | 0.15 | 1.51825 | 63.93 |
| 7 | ∞ | 0.30 | 1.51825 | 63.93 |
| 8 | ∞ | 0.00 | | |

-continued

Unit mm

| Surface no. | r | d | ne | ve |
|---|---|---|---|---|
| Image plane | ∞ | | | |ыми
| Various data | | | | |
| D0 | | 6 | | |
| f | | 0.317 | | |
| FNO. | | 4.088 | | |
| IH | | 0.242 | | |
| 2ω | | 90.77 | | |
| Lt | | 1 | | |
| Dp | | 0.62 | | |

Example 4

Unit mm

| Surface no. | r | d | ne | ve |
|---|---|---|---|---|
| Surface data | | | | |
| 1 | ∞ | 0.25 | 1.88815 | 40.52 |
| 2 | ∞ | 0.00 | | |
| 3 (Stop) | ∞ | 0.00 | | |
| 4 | ∞ | 0.27 | 2.00912 | 28.92 |
| 5 | −0.305 | 0.02 | | |
| 6 | ∞ | 0.15 | 1.51825 | 63.93 |
| 7 | ∞ | 0.30 | 1.51825 | 63.93 |
| 8 | ∞ | 0.00 | | |
| Image plane | ∞ | | | |
| Various data | | | | |
| D0 | | 5 | | |
| f | | 0.302 | | |
| FNO. | | 3.906 | | |
| IH | | 0.242 | | |
| 2ω | | 95.37 | | |
| Lt | | 0.99 | | |
| Dp | | 0.62 | | |

Example 5

Unit mm

| Surface no. | r | d | ne | ve |
|---|---|---|---|---|
| Surface data | | | | |
| 1 | ∞ | 0.25 | 1.88815 | 40.52 |
| 2 | ∞ | 0.00 | | |
| 3 (Stop) | ∞ | 0.00 | | |
| 4 | ∞ | 0.23 | 1.88815 | 40.52 |
| 5 | −0.305 | 0.10 | | |
| 6 | ∞ | 0.30 | 1.51825 | 63.93 |
| 7 | ∞ | 0.00 | | |
| Image plane | ∞ | | | |
| Various data | | | | |
| D0 | | 5 | | |
| f | | 0.287 | | |
| FNO. | | 3.709 | | |
| IH | | 0.196 | | |
| 2ω | | 79 | | |
| Lt | | 0.88 | | |
| Dp | | 0.52 | | |

The values of the conditional expressions in each example are listed below.

| Conditional expression | Example1 | Example2 | Example3 |
|---|---|---|---|
| (1) IH/Dp | 0.39 | 0.39 | 0.39 |
| (2) $1 + Dp \times \omega r/(2 \times IH)$ | 1.884 | 1.947 | 2.015 |
| (3) $NL/(1 + Dp \times \omega r/(2 \times IH))$ | 0.985 | 0.981 | 0.973 |
| (4) Np | 1.88815 | 1.88815 | 1.88815 |
| (5) Tp/Dp | 0.403 | 0.403 | 0.403 |

| Conditional expression | Example4 | Example5 |
|---|---|---|
| (1) IH/Dp | 0.39 | 0.377 |
| (2) $1 + Dp \times \omega r/(2 \times IH)$ | 2.066 | 1.915 |
| (3) $NL/(1 + Dp \times \omega r/(2 \times IH))$ | 0.972 | 0.986 |
| (4) Np | 1.88815 | 1.88815 |
| (5) Tp/Dp | 0.403 | 0.481 |

Figure 8A:
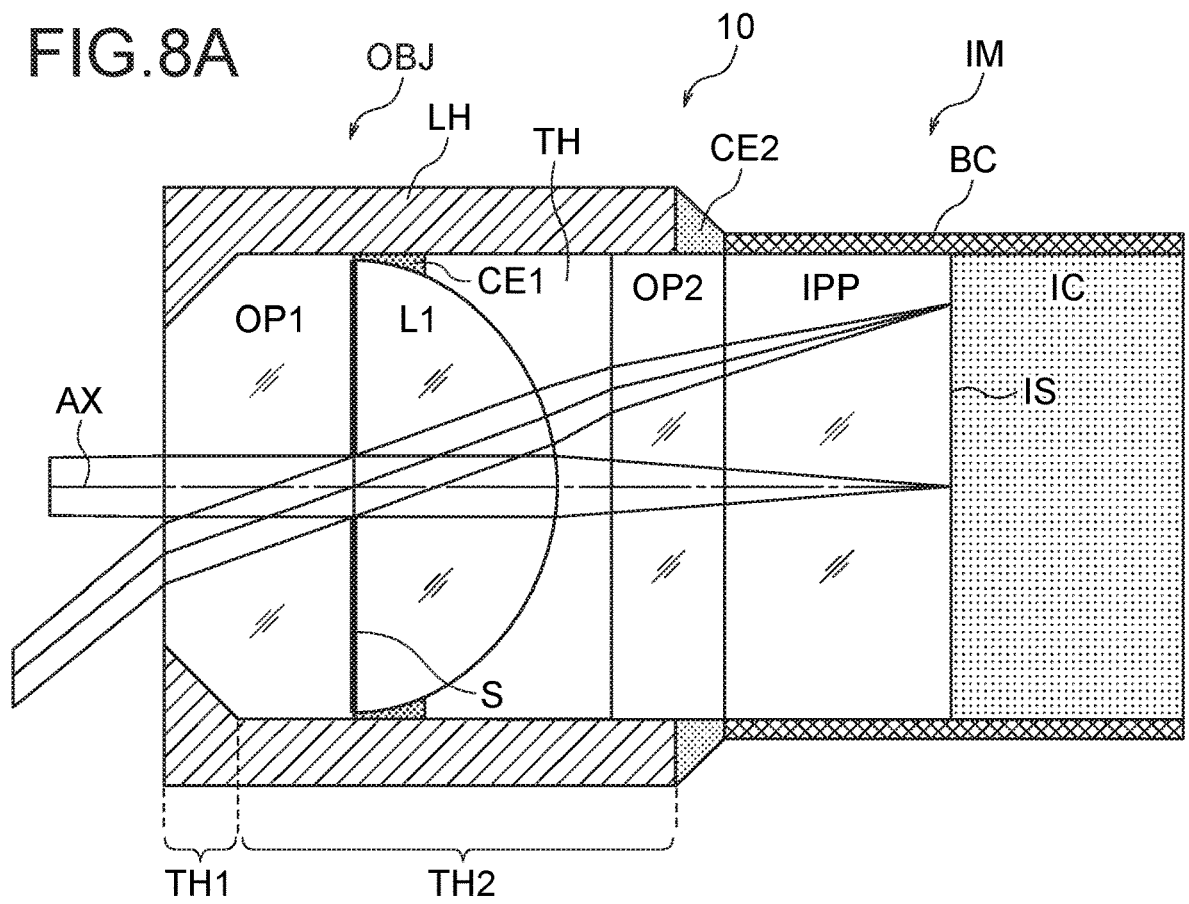
FIGS. 8A and 8B are diagrams showing optical apparatuses according to the embodiment.
Figure 8B:
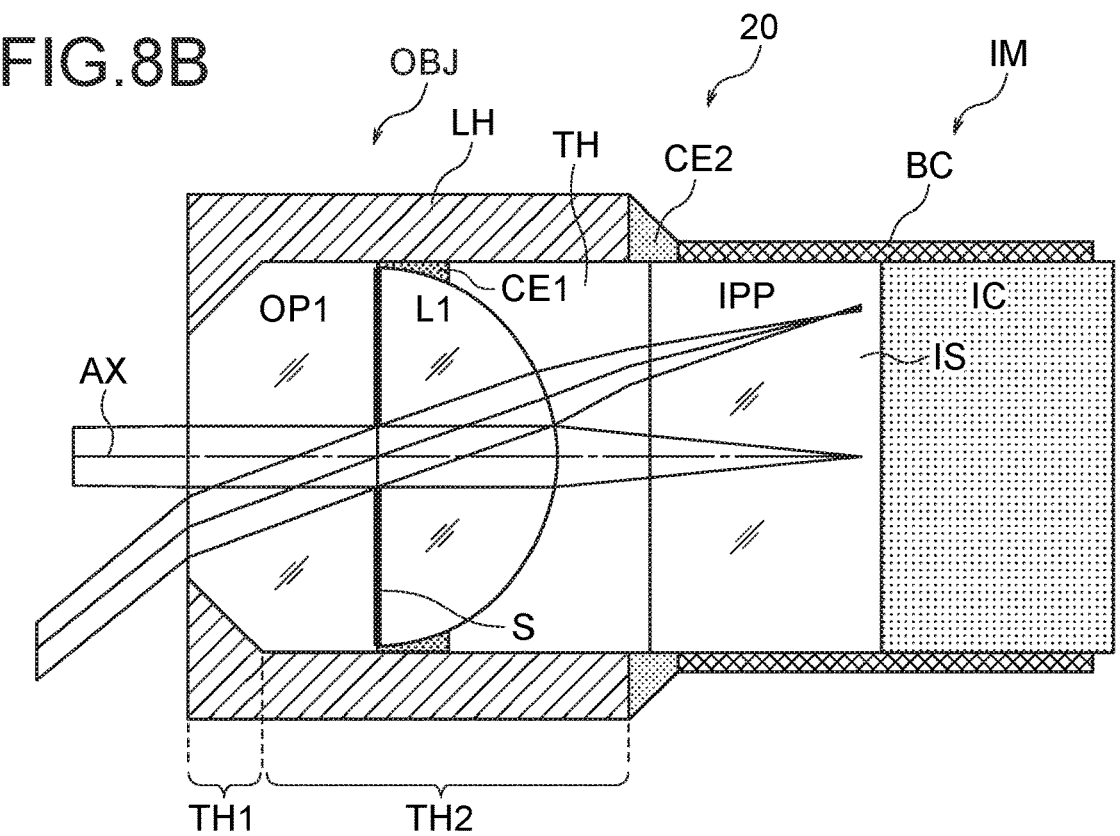

FIGS. 8A and 8B are diagrams showing optical systems according to the embodiment. FIG. 8A shows a first exemplary optical apparatus. FIG. 8B shows a second exemplary optical apparatus. The FIGS. 8A and 8B show structures that hold an objective optical system and an imager.

FIG. 8A shows the first exemplary optical apparatus. The first exemplary optical apparatus 10 is an image pickup apparatus or an endoscope. The optical apparatus 10 has an objective optical system OBJ. The objective optical system OBJ includes a flat plate OP1, an aperture stop S, and a planoconvex lens L1. The flat plate OP1 and the planoconvex lens L1 are cemented together with the aperture stop S between.

The edge of the non-cemented surface of the flat plate OP1 is chamfered, but the edge of its cemented surface is not chamfered. The outer circumference of the flat plate OP1 on the non-cemented surface side has a shape like the side surface of a truncated cone. The outer circumference of the flat plate OP1 on the cemented surface side has a shape like the side surface of a cylinder.

The optical apparatus 10 has a lens frame LH having a through bore TH. The through bore TH is composed of a first space TH1 and a second space TH2. The first space TH1 has the shape of a truncated cone. The second space TH2 has the shape of a cylinder.

The lens frame LH has an inner circumferential surface. The inner circumferential surface is composed of the side surface of the truncated cone of the first space TH1 and the side surface of the cylinder of the second space TH2.

Fixation of Objective Optical System

The size of the truncated cone of the first space TH1 is larger than the size of the truncated cone of the flat plate OP1. The size of the cylinder of the second space TH2 is larger than the size of the cylinder of the flat plate OP1.

The side surface of the truncated cone of the first space TH1 is substantially the same as the side surface of the truncated cone of the flat plate OP1. The side surface of the cylinder of the second space TH2 is substantially the same as the side surface of the cylinder of the flat plate OP1.

The outer diameter of the planoconvex lens L1 is smaller than the outer diameter of the flat plate OP1. Hence, it is possible to insert the objective optical system OBJ into the through bore TH. When the objective optical system OBJ is received in the through bore TH, the flat plate OP1 is positioned in the first space TH1 and the second space TH2, and the planoconvex lens L1 is positioned in the second space TH2.

The through bore TH and the flat plate OP1 can be produced with high precision. Hence, the tolerance is set such that the gap left between the outer circumferential surface of the flat plate OP1 and the inner circumferential surface of the lens frame LH is made very small. The gap between the outer circumferential surface of the flat plate OP1 and the inner circumferential surface of the lens frame LH is filled with adhesive CE1 all along the circumference to achieve the liquid-tightness after the adhesion.

The planoconvex lens L1 and the flat plate OP1 is cemented such that the optical axis of the planoconvex lens L1 substantially coincides with the center of the flat plate OP1. In consequence, when the outer circumferential surface of the flat plate OP1 is in contact with the inner circumferential surface of the lens frame LH, the optical axis AX of the objective optical system OBJ and the center axis of the through bore TH substantially coincide with each other.

When the flat plate OP1 is positioned in the first space TH1, a space is formed between the non-cemented surface of the planoconvex lens L1 and the inner circumferential surface of the lens frame LH. This space serves as a space for allowing spilling-out of the adhesive CE1. Thus, the objective optical system OBJ can be fixed to the lens frame LH.

The planoconvex lens L1 does not have an outer circumferential surface extending between the object side surface and the image side surface. Therefore, it is not possible to hold the planoconvex lens L1 by its outer circumferential surface.

However, the planoconvex lens L1 is cemented to the flat plate OP1. The flat plate OP1 has the outer circumferential surface having the shape of a cylinder extending between the object side surface and the image side surface. The flat plate OP1 can be held easily by this outer circumferential surface. Therefore, the operation of adhering and fixing the objective optical system. OBJ can be made simple, even though the size of the objective optical system OBJ is small.

Fixation of Imager

The optical apparatus 10 may include an imager IM. The imager IM picks up an optical image formed by the objective optical system. OBJ. Thus, optical image data can be obtained.

The imager IM has an image pickup chip IC and a flat plate IPP. The image pickup chip IC has an image pickup surface IS. The flat plate IPP is a flat plate provided for the purpose of sealing. The flat plate IPP provides protection for the image pickup surface IS.

The outer circumference of the imager IM is covered with a light blocking material BC. The light blocking material BC can protect the imager chip IC and the flat plate IPP.

The flat plate IPP is transparent, and light enters the flat plate IPP through its outer circumferential surface. If such light is incident on the image pickup surface IS, flare will result. Covering the outer circumferential surface of the flat plate IPP with the light blocking material BC can prevent the light from entering through the outer circumferential surface of the flat plate IPP. This can prevent the occurrence of flare.

In the case where the imager IM is employed to pick up optical images, it is preferred that the imager IM be held by the lens frame LH. In a plane perpendicular to the optical axis AX, the contour of the imager IM is rectangular, while the contour of the through bore TH is circular. Thus, the contour of the imager IM and the contour of the through bore TH are different from each other.

To compromise the difference, the optical apparatus 10 uses a flat plate OP2. The imager IM is held on the lens frame LH indirectly using the flat plate OP2.

The flat plate IPP is adhered to the flat plate OP2. The flat plate IPP is integrated with the image pickup chip IC. The imager IM can be fixed to the flat plate OP2 by adhering the flat plate OP2 and the flat plate IPP.

The shape of the flat plate is a cylinder. Hence, the contour of the flat plate OP2 is circular in a plane perpendicular to the optical axis AX. As described above, the contour of the through bore TH is circular. Therefore, if the diameter of the flat plate OP2 is made smaller than the diameter of the through bore TH, the flat plate OP2 can be inserted in the through bore TH. When the flat plate OP2 is received in the through bore TH, the flat plate OP2 is positioned in the second space TH2.

The flat plate OP2 can be produced with high precision. The outer diameter of the flat plate OP2 is equal to the outer diameter of the cemented side surface of the flat plate OP1. As described above, the tolerance is set such that the gap left between the outer circumferential surface of the flat plate OP1 and the inner circumferential surface of the lens frame LH is made very small. Hence, when the flat plate OP2 is positioned in the second space TH2, the outer circumferential surface of the flat plate OP2 is nearly in contact with the inner circumferential surface of the lens frame LH.

The flat plate IPP and the flat plate OP2 are cemented together such that the center of the image pickup surface IS coincides with the center of the flat plate OP2. In consequence, when the outer circumferential surface of the flat plate OP2 is nearly in contact with the inner circumferential surface of the lens frame LH, the center of the image pickup surface IS is positioned substantially on the center axis of the through bore TH.

As above, the eccentricity between the optical axis AX of the objective optical system OBJ and the center axis of the through bore TH can be kept sufficiently small. In consequence, when the flat plate OP2 is inserted in the lens frame LH, the eccentricity between the center of the image pickup surface IS and the optical axis AX of the objective optical system OBJ can also be kept sufficiently small.

The optical apparatus 10 picks up an optical image formed by the objective optical system OBJ using the imager IM. To pick up an optical image, it is necessary that the position of the image pickup surface IS be coincide with the position of the image plane of the objective optical system OBJ. The position of the image pickup surface IS can be changed by moving the imager IM along the optical system.

The imager IM is fixed to the flat plate OP2. It is possible to move the imager IM along the optical axis AX by moving the flat plate OP2 relative to the lens frame LH. The flat plate OP2 moves with its outer circumferential surface being in contact with the inner circumferential surface of the lens frame LH. Thus, the imager IM can be moved smoothly.

The adjustment of the position of the image pickup surface IS may be performed based on an image picked up by the imager IM. For example, a chart may be provided on the object side of the objective optical system OBJ. An optical image of the chart is formed on the image plane of the objective optical system OBJ. This optical image is picked up by the imager chip IC. Thus, an image of the chart is obtained.

As the position of the image pickup surface IS approaches the position of the image plane of the objective optical system OBJ, the image of the chart becomes sharper. The position of the image pickup surface IS may be changed to find the position that makes the image of the chart sharpest, and the imager IM may be fixed at the position that makes the image of the chart sharpest.

As described above, the flat plate OP2 is positioned in the second space TH2. When the flat plate OP2 is positioned in the second space TH2, a space is formed between the lens frame LH and the light blocking material BC. This space may be filled with an appropriate quantity of adhesive CE2, and the adhesive CE2 is cured. Thus, the imager IM is fixed to the lens frame LH.

The imager IM is held on the lens frame LH by the flat plate OP2. Therefore, the contour of the imager IM is not limited to rectangular. If the contour of the imager IM is rectangular, it may be either oblong or square. The diagonal length of the image pickup surface IS may be shorter than the diameter of the flat plate OP2.

The second exemplary optical apparatus is shown in FIG. 8B. The components of the second exemplary optical apparatus that are the same as those in the first exemplary optical apparatus will be denoted by the same reference signs and will not be described further.

The second exemplary optical apparatus 20 is an image pickup apparatus or an endoscope. The optical apparatus 20 has an objective optical system OBJ. The objective optical system OBJ includes a flat plate OP1, an aperture stop S, and a planoconvex lens L1. The flat plate OP1 and the planoconvex lens L1 are cemented together with the aperture stop S between.

The optical apparatus 20 may have an imager IM. The imager IM picks up an optical image formed by the objective optical system. OBJ. Thus, optical image data can be obtained.

In the case of this optical system 20, the imager IM is directly held on the lens frame LH. Hence, the optical apparatus 20 does not use a flat plate like the flat plate OP2 used in the first exemplary optical apparatus 10.

The contour of the imager IM is oblong. The cross section shown in FIG. 8B is a plane parallel to the plane containing a short side. As shown in FIG. 8B, the length of the short side of the imager IM is equal to the diameter of the through bore TH. The length of the long side of the imager IM is larger than the diameter of the through bore TH.

Along the long side of the imager IM, the flat plate IPP is partly in contact with the lens frame LH. Hence, the flat plate IPP is shifted in a plane perpendicular to the optical axis AX so as to locate the center of the image pickup surface IS on the center axis of the through bore TH.

When the center of the image pickup surface IS is located on the center axis of the through bore TH, the imager IM is temporarily fixed. In this state, an appropriate quantity of adhesive CE2 is supplied to the portion where the lens frame LH and the light blocking material BC are opposed to each other, and then the adhesive CE2 is cured. The imager IM can be fixed to the lens frame LH in this way.

The optical apparatus 20 does not use a flat plate like the flat plate OP2 used in the first exemplary optical apparatus 10. Therefore, the number of components used can be made smaller than that of the first exemplary optical system 10. This can lead to reduction in the size and cost.

The contour of the imager IM may be square. In the case where its diagonal length is larger than the diameter of the through bore TH, the imager IM can be fixed to the lens frame LH in the same manner as in the case where the contour of the imager IM is oblong.

In the case where its diagonal length is equal to the diameter of the through bore LH, the imager IM is fixed to the lens frame LH by the light blocking material BC. Then, it is necessary that the light blocking material BC have a sufficiently large width and a sufficient strength.

The optical apparatus of this embodiment can be used in an ultrasonic endoscope. Ultrasonic endoscopes have an ultrasonic transducer and an objective optical system provided in the distal end portion of its insert part. The ultrasonic transducer outputs an ultrasonic image signal. The ultrasonic image signal is transformed into an image by the ultrasonic observation apparatus. The ultrasonic image created by the ultrasonic observation apparatus is displayed on a video monitor.

The objective optical system forms an optical image. This optical image is picked up by the imager. The imager outputs an optical image signal. The optical image signal is transformed into an image by the endoscope observation apparatus. The optical image created by the endoscope observation apparatus is displayed on the video monitor.

It is important for ultrasonic endoscopes that it can obtain high quality ultrasonic images. On the other hand, the optical image is used to see, for example, the direction of move of the insert part and the site to which ultrasonic waves are emitted. Therefore, it is sufficient that the optical image has an image quality that does not cause difficulties in observing it.

The objective optical system of this embodiment can form optical images that can be observed without difficulties, though it is small in size. As above, the optical apparatus of this embodiment can obtain high quality ultrasonic images and optical images with an image quality that does not cause difficulties in observing them.

In the following, designing, production, and assembly of the lens will be described.

(Designing and Production of Planoconvex Lens)

In the optical apparatuses 10 and 20, the objective optical system OBJ is held on the lens frame LH by the flat plate OP1. Hence, when designing the objective optical system OBJ, it is preferred to determine the outer diameter Dp of the flat plate OP1 firstly.

The contour or the outer shape of the planoconvex lens L1 is substantially the same of the contour of the flat plate OP1. The shape of the planoconvex lens L1 is substantially hemispherical. Therefore, if the outer diameter of the flat plate OP1 is Dp, the image side surface of the planoconvex lens L1 is a convex surface having a curvature radius of Dp/2 or a convex surface having a curvature radius close to Dp/2.

The planoconvex lens L1 can be produced by surface-grinding a ball lens. The planoconvex lens L1 can be shaped only by surface-grinding a ball lens.

This means that centering and edging is not performed in producing the planoconvex lens L1. Therefore, the process of producing the lens can be made simple. Simplification of the lens production process can be achieved even in the case of ball lenses with extremely small sizes.

The planoconvex lens L1 is a glass lens. Hence, a ball lens of a glass material is used to produce the planoconvex lens L1. The ball lens may be one available in the market. For example, extremely small ball lenses having diameter of 0.5 mm or 0.3 mm are commercially available.

(Production of Objective Optical System)

The outer diameter of the planoconvex lens L1 is substantially equal to the outer diameter of the flat plate OP1. Hence, the objective optical system OBJ can be produced only by aligning the outer circumference of the flat plate OP1 and the outer circumference of the planoconvex lens L1 with each other and then cementing the flat plate OP1 and the planoconvex lens L1 together.

In the case where the outer diameter of the planoconvex lens L1 and the outer diameter of the flat plate OP1 are equal, the flat plate OP1 and the planoconvex lens L1 may be positioned such that the entire circumference of the flat plate OP1 and the entire circumference of the planoconvex lens L1 are aligned with each other.

Due to the presence of production errors, the outer diameter of the flat plate OP1 and the outer diameter of the planoconvex lens L1 are not always equal to each other. Therefore, the tolerance should be set such that the difference in their outer diameters is kept sufficiently small. In the case where a small difference in their outer diameters is intentionally set, it is preferred that the outer diameter of the flat plate OP1 be made larger than the outer diameter of the planoconvex lens L1, because this will make the flat plate OP1 easy to hold in assembly.

In the case where the outer diameter of the planoconvex lens L1 and the outer diameter of the flat plate OP1 are different from each other, the flat plate OP1 and the planoconvex lens L1 may be positioned such that the circumference of the flat plate OP1 and the circumference of the planoconvex lens L1 are partly aligned with each other. In this case, the difference in their outer diameters will lead to eccentricity. This eccentricity can be made small by making the difference in their outer diameters sufficiently small.

Since both the surfaces of the flat plate OP1 are flat, the flat plate OP1 does not have refractive power. The planoconvex lens L1 is cemented to the flat plate OP1 having no refractive power. Therefore, even if a displacement between the flat plate OP1 and the planoconvex lens L1 occurs in a plane perpendicular to the optical axis AX, aberrations do not get worse. Therefore, eccentricity caused in cementing does not matter in the production of the objective optical system OBJ.

(Assembly)

In the case where the planoconvex lens L1 is not cemented to the flat plate OP1, the flat plate OP1 is firstly brought to the inlet opening of the through bore TH. The outer circumferential surface of the flat plate OP1 has the shape of the side surface of a cylinder. Hence, the flat plate OP1 is easy to hold, and the flat plate OP1 can be brought easily.

After the flat plate OP1 is brought as above, the flat plate OP1 is inserted into the through bore TH. In consequence, the flat plate OP1 is placed in a desired position. After the flat plate OP1 is placed in position, the planoconvex lens L1 is brought to the inlet opening of the through bore TH.

The planoconvex lens L1 does not have an outer circumferential surface shaped like the side surface of a cylinder. Hence the planoconvex lens L1 is not easy to hold, and the planoconvex lens L1 cannot be brought easily.

Even if the planoconvex lens L1 is inserted into the through bore TH, it is not easy to place the planoconvex lens L1 in a desired position. For this reason, it is difficult to position the planoconvex lens L1 relative to the flat plate OP1 precisely.

In the case where the planoconvex lens L1 is cemented to the flat plate OP1, the flat plate OP1 and the planoconvex lens L1 can be brought to the inlet opening of the through bore TH together. Since the flat plate OP1 has an outer circumferential surface shaped like the side surface of a cylinder, the flat plate OP1 and the planoconvex lens L1 can be held easily by the outer circumferential surface of the flat plate OP1, and the flat plate OP1 and the planoconvex lens L1 can be brought easily.

After the flat plate OP1 and the planoconvex lens L1 are brought as above, the flat plate OP1 and the planoconvex lens L1 are inserted into the through bore TH. In consequence, the flat plate OP1 is placed in a desired position. As the planoconvex lens L1 is cemented to the flat plate OP1, the planoconvex lens L1 is also placed in a desired position.

As above, in the case where the planoconvex lens L1 is cemented to the flat plate OP1, it is easy to bring the planoconvex lens L1 and to place it in a desired position.

The positioning or alignment of the planoconvex lens L1 relative to the flat plate OP1 is done precisely at the time of cementing them. together. Therefore, it is not necessary to position the planoconvex lens L1 relative to the flat plate OP1 after insertion into the through bore TH.

(Estimated Refractive Index of Planoconvex Lens)

Conditional expression (2) may be regarded as a conditional expression relating to the estimated refractive index of the planoconvex lens. The estimated refractive index is a refractive index that can be practically selected as the refractive index of the planoconvex lens. The estimated refractive index can be calculated from the largest image height IH, the angle of view ωr, and the outer diameter Dp of the flat plate.

Conditional expression (2) contains the angle of view ωr. The angle of view ωr is a parameter relating to the half angle of view ω. The angle of view ωr is an angle of view expressing the absolute value of the half angle of view ω by radian. The largest image height and the angle of view are optical specifications. The outer diameter of the flat plate is a design parameter.

The largest image height, the angle of view, and the outer diameter of the flat plate are determined independently from the planoconvex lens. In the objective optical system of this embodiment, there is the constraint that the curvature radius of the convex surface of the planoconvex lens is substantially equal to half the outer diameter of the flat plate. With this constraint, an appropriate refractive index of the planoconvex lens can be estimated from the largest image height, the angle of view, and the outer diameter of the flat plate.

The estimated refractive index n of the planoconvex lens is expressed by the following equation:

$$n = 1 + Dp \times \omega r / (2 \times IH).$$

The estimated refractive index n can be calculated by eliminating the curvature radius R and the focal length f in the following equations (A), (B), and (C):

$$|R| = Dp/2 \tag{A}$$

$$f = |R|/(n-1) \tag{B}$$

$$IH = f \times \omega r \tag{C},$$

where $\omega r = 2\pi \times |\omega|/360°$, R is the curvature radius of the convex surface of the planoconvex lens, Dp is the outer diameter of the flat plate, f is the focal length of the objective optical system, IH is the largest image height, and ω is the half angle of view.

Equation (A) is formulated for a representative case based on the assumption that the planoconvex lens is a hemisphere having a diameter equal to the diameter of the flat plate. Equation (B) is an equation expressing the focal length. Equation (C) is a projection equation formulated for a representative case based on the assumption that the relationship between the image height IH and the half angle of view ω is linear.

As above, while equation (B) is a physically strict equation, equations (A) and (C) are based on representative assumptions, which are not intended to be physically correct. The estimated refractive index n calculated from a set of equations including equations (A) and (C) is a mere estimated value.

As above, the present invention can suitably be applied to objective optical systems that are required to be small in size, easy to produce and capable of forming optical images that can be observed without difficulties. The present invention can also suitably be applied to image pickup apparatuses and endoscopes that are required to obtain images having an image quality that does not cause difficulties in observing them.

The present invention can provide an objective optical system that is easy to produce and capable of forming optical images that can be observed without difficulties while it is small in size. The present invention can also provide an image pickup apparatus and an endoscope that can obtain images having an image quality that does not cause difficulties in observing them.

What is claimed is:

1. An objective optical system comprising, in order from the object side:
   a flat plate;
   an aperture stop; and
   a substantially hemispherical planoconvex lens having an outer diameter substantially equal to the outer diameter of the flat plate,
   wherein the flat plate and the planoconvex lens are cemented together with the aperture stop between, and the objective optical system satisfies the following conditional expressions (1), (2), and (3):

$$0.3 < IH/Dp < 0.45 \tag{1}$$

$$1.7 < 1 + Dp \times \omega r/(2 \times IH) < 2.1 \tag{2}$$

$$0.9 < NL/(1 + Dp \times \omega r/(2 \times IH)) < 1.1 \tag{3}$$

where $\omega r = 2 \times \pi \times |\omega|/360°$, IH is the largest image height, Dp is the outer diameter of the flat plate, $\omega$ is the half angle of view, and NL is the refractive index of the planoconvex lens.

2. An objective optical system according to claim 1, wherein the objective optical system satisfies the following conditional expressions (4) and (5):

$$1.7 < Np \tag{4}$$

$$0.3 < Tp/Dp < 0.7 \tag{5}$$

where Np is the refractive index of the flat plate, Tp is the thickness of the flat plate on the optical axis, and Dp is the outer diameter of the flat plate.

3. An objective optical system according to claim 1, wherein the objective optical system satisfies the following conditional expression (6):

$$75° \leq \theta \leq 105° \tag{6},$$

where $\theta$ is the magnitude of the angle formed by the optical axis and the straight line connecting a point on the outer circumference of the object side surface of the planoconvex lens and the center of curvature of the image side surface.

4. An objective optical system according to claim 1, wherein the aperture stop has a light transmitting portion and a light blocking portion formed by a light blocking film.

5. An objective optical system according to claim 1, wherein the aperture stop is provided on the image side surface of the flat plate or the object side surface of the planoconvex lens.

6. An objective optical system according to claim 1, wherein the F-number of the objective optical system is equal to or larger than 3.5.

7. An image pickup apparatus comprising an objection optical system, the objective optical system comprising, in order from the object side:
   a flat plate;
   an aperture stop; and
   a substantially hemispherical planoconvex lens having an outer diameter substantially equal to the outer diameter of the flat plate,
   wherein the flat plate and the planoconvex lens are cemented together with the aperture stop between, and the objective optical system satisfies the following conditional expressions (1), (2), and (3):

$$0.3 < IH/Dp < 0.45 \tag{1}$$

$$1.7 < 1 + Dp \times \omega r/(2 \times IH) < 2.1 \tag{2}$$

$$0.9 < NL/(1 + Dp \times \omega r/(2 \times IH)) < 1.1 \tag{3}$$

where $\omega r = 2 \times \pi \times |\omega|/360°$, IH is the largest image height, Dp is the outer diameter of the flat plate, $\omega$ is the half angle of view, and NL is the refractive index of the planoconvex lens.

8. An image pickup apparatus according to claim 7, wherein the objective optical system satisfies the following conditional expressions (4) and (5):

$$1.7 < Np \tag{4}$$

$$0.3 < Tp/Dp < 0.7 \tag{5}$$

where Np is the refractive index of the flat plate, Tp is the thickness of the flat plate on the optical axis, and Dp is the outer diameter of the flat plate.

9. An image pickup apparatus according to claim 7, wherein the objective optical system satisfies the following conditional expression (6):

$$75° \leq \theta \leq 105° \tag{6},$$

where $\theta$ is the magnitude of the angle formed by the optical axis and the straight line connecting a point on the outer circumference of the object side surface of the planoconvex lens and the center of curvature of the image side surface.

10. An image pickup apparatus according to claim 7, wherein the aperture stop has a light transmitting portion and a light blocking portion formed by a light blocking film.

11. An image pickup apparatus according to claim 7, wherein the aperture stop is provided on the image side surface of the flat plate or the object side surface of the planoconvex lens.

12. An objective optical system according to claim 7, wherein the F-number of the objective optical system is equal to or larger than 3.5.

13. An endoscope comprising an objection optical system, the objective optical system comprising, in order from the object side:
    a flat plate;
    an aperture stop; and
    a substantially hemispherical planoconvex lens having an outer diameter substantially equal to the outer diameter of the flat plate,
    wherein the flat plate and the planoconvex lens are cemented together with the aperture stop between, and the objective optical system satisfies the following conditional expressions (1), (2), and (3):

$$0.3 < IH/Dp < 0.45 \tag{1}$$

$$1.7 < 1 + Dp \times \omega r/(2 \times IH) < 2.1 \tag{2}$$

$$0.9 < NL/(1 + Dp \times \omega r/(2 \times IH)) < 1.1 \tag{3}$$

where $\omega r = 2 \times \pi \times |\omega|/360°$, IH is the largest image height, Dp is the outer diameter of the flat plate, $\omega$ is the half angle of view, and NL is the refractive index of the planoconvex lens.

14. An endoscope according to claim 13, wherein the objective optical system satisfies the following conditional expressions (4) and (5):

$$1.7 < Np \qquad (4)$$

$$0.3 < Tp/Dp < 0.7 \qquad (5)$$

where Np is the refractive index of the flat plate, Tp is the thickness of the flat plate on the optical axis, and Dp is the outer diameter of the flat plate.

15. An endoscope according to claim 13, wherein the objective optical system satisfies the following conditional expression (6):

$$75° \leq \theta \leq 105° \qquad (6),$$

where $\theta$ is the magnitude of the angle formed by the optical axis and the straight line connecting a point on the outer circumference of the object side surface of the planoconvex lens and the center of curvature of the image side surface.

16. An endoscope according to claim 13, wherein the aperture stop has a light transmitting portion and a light blocking portion formed by a light blocking film.

17. An endoscope according to claim 13, wherein the aperture stop is provided on the image side surface of the flat plate or the object side surface of the planoconvex lens.

18. An endoscope according to claim 13, wherein the F-number of the objective optical system is equal to or larger than 3.5.

* * * * *